(12) United States Patent
Tomitaka et al.

(10) Patent No.: US 10,561,745 B2
(45) Date of Patent: Feb. 18, 2020

(54) STIMULI-RESPONSIVE MAGNETO-PLASMONIC NANOCARRIER

(71) Applicants: Asahi Tomitaka, Miami, FL (US); Madhavan Nair, Coral Gables, FL (US)

(72) Inventors: Asahi Tomitaka, Miami, FL (US); Madhavan Nair, Coral Gables, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 0 days.

(21) Appl. No.: 15/471,719

(22) Filed: Mar. 28, 2017

(65) Prior Publication Data
US 2018/0280546 A1    Oct. 4, 2018

(51) Int. Cl.
| | |
|---|---|
| *A61K 49/18* | (2006.01) |
| *A61K 49/00* | (2006.01) |
| *A61K 41/00* | (2006.01) |
| *A61K 47/69* | (2017.01) |
| *A61K 49/04* | (2006.01) |
| *A61K 9/127* | (2006.01) |
| *A61K 9/00* | (2006.01) |

(52) U.S. Cl.
CPC .......... *A61K 49/0002* (2013.01); *A61K 9/127* (2013.01); *A61K 41/00* (2013.01); *A61K 47/6923* (2017.08); *A61K 47/6929* (2017.08); *A61K 49/0065* (2013.01); *A61K 49/0093* (2013.01); *A61K 49/0423* (2013.01); *A61K 49/183* (2013.01); *A61K 9/0019* (2013.01)

(58) Field of Classification Search
CPC ......... A61K 49/18; A61K 47/69; A61K 41/00
See application file for complete search history.

(56) References Cited

U.S. PATENT DOCUMENTS

| | | | | |
|---|---|---|---|---|
| 8,563,043 B2* | 10/2013 | Medarova | .......... | A61K 41/0052 424/489 |
| 9,789,154 B1* | 10/2017 | Vo-Dinh | ................ | A61K 38/02 |
| 2005/0025969 A1* | 2/2005 | Berning | ................ | B22F 1/0018 428/403 |
| 2006/0171894 A1* | 8/2006 | Takeyama | ............ | A61K 49/183 424/9.32 |
| 2014/0234429 A1* | 8/2014 | Mahmoudi | ............... | A61K 9/14 424/490 |

FOREIGN PATENT DOCUMENTS

WO    WO2014085651    *    6/2014

OTHER PUBLICATIONS

Zhichuan Xu et al. Magnetic Core/Shell Fe3O4/Au and Fe3O4? Au?Ag Nanoparticles with Tunable Plasmonic Properties, J. Am. Chem. Soc. 2007, 129, 8698-8699.*

Hyon-Min Song et al. Plasmon-Resonant Nanoparticles and Nanostars with Magnetic Cores: Synthesis and Magnetomotive Imaging, ACS Nano 4(9), 5163-5173. (Year: 2010).*

Paresh Chandra Ray et al., Theranostic Magnetic Cor-Plasmonic Shell Star Shape Nanoparticle for the Isolation of Targeted Rare Tumor Cells from Whole Blood, Fluorescence Imaging, and Photothermal Destruction of Cancer, Molecular Pharmaceutics, 10, 857-866. (Year: 2013).*

Zhichuan Xu et al., Magnetic Core/Shell Fe3O4/Au and Fe3O4/Ag Nanoparticles with Tunable Plasmonic Properties, JACS, 129, 8698-8699. (Year: 2007).*

Pedro Quaresma et al., Star-shaped magnetite @gold nanoparticles for protein magnetic separation and SERS detection, RSC Adv . 4, 3659. (Year: 2014).*

Elyahb Allie Kwizera et al., Size- and shape-controlled synthesis and properties of Magnetic-plasmonic core-shell Nanoparticles, J Phys Chem Nanomater Interfaces, 120(19), 10530-10546. (Year: 2016).*

Abakumov, M.A. et al., "VEGF-Targeted Magnetic Nanoparticles for MRI Visualization of Brain Tumor." *Nanomedicine*, May 2015, 11:825-833, doi: 10.1016/j.nano.2014.12.011.

Ballabh, P. et al., "The Blood-Brain Barrier: An Overview, Structure, Regulation, and Clinical Implications." *Neurobiology of Disease*, Jun. 2004, 16(1):1-13, doi: 10.1016/j.nbd.2003.12.016.

Berkowitz, A.E. et al., "Influence of Crystallite Size on the Magnetic Properties of Acicular $\gamma$—$Fe_2O_3$ Particles." *Journal of Applied Physics*, Feb. 1968, 39(2):1261-1263, doi: 10.1063/1.1656256.

Brown, K.R., Natan, M.J., "Hydroxylamine Seeding of Colloidal Au Nanoparticles in Solution and on Surfaces." *Langmuir*, Jan. 1998, 14:726-728, doi: 10.1021/la970982u.

Brown, K.R. et al., "Seeding of Colloidal Au Nanoparticle Solutions. 2. Improved Control of Particle Size and Shape." *Chem. Mater.*, 2000, 12(2):306-313, doi: 10.1021/cm980065p.

Chen, J. et al., "Reducible Polyamidoamine-Magnetic Iron Oxide Self-Assembled Nanoparticles for Doxorubicin Delivery." *Biomaterials*, Jan. 2014, 35(4):1240-1248, doi: 10.1016/j.biomaterials.2013. 10.057.

Cheng, K.K. et al., "Curcumin-Conjugated Magnetic Nanoparticles for Detecting Amyloid Plaques in Alzheimer's Disease Mice Using Magnetic Resonance Imaging (MRI)." *Biomaterials*, Mar. 2015, 44:155-172, doi: 10.1016/j.biomaterials.2014.12.005.

Ding, H. et al., "Enhanced Blood-Brain Barrier Transmigration Using a Novel Transferrin Embedded Fluorescent Magneto-Liposome Nanoformulation." *Nanotechnology*, Jan. 2014, 25:1-14, doi: 10.1088/09574484/25/5/055101.

(Continued)

*Primary Examiner* — Michael G. Hartley
*Assistant Examiner* — Jagadishwar R Samala
(74) *Attorney, Agent, or Firm* — Saliwanchik, Lloyd & Eisenschenk

(57) ABSTRACT

Materials and methods for synthesizing magnetic core/gold shell nanoparticles and magneto-plasmonic nanostars are provided. Formulations comprising nanoparticles optionally bound to or co-loaded with a therapeutic agent encapsulated within liposomes are provided. A method for treating diseases (e.g., brain diseases) in a subject by administering to the subject a formulation comprising the nanoparticle formulation is also provided. Further, a method is provided for imaging a target site of a subject following the administering of the nanoparticle formulations.

19 Claims, 9 Drawing Sheets

(56) References Cited

OTHER PUBLICATIONS

Eustis, S., El-Sayed, M.A., "Why Gold Nanoparticles are More Precious Than Pretty Gold: Noble Metal Surface Plasmon Resonance and its Enhancement of the Radiative and Nonradiative Properties of Nanocrystals of Different Shapes." *Chemical Society Reviews*, Apr. 2006, 35:209-217, doi: 10.1039/b514191e.

Frens, G., "Controlled Nucleation for the Regulation of the Particle Size in Monodisperse Gold Suspensions." *Nature Physical Science*, Jan. 1973, 241:Abstract.

Goia, D.V., Matijević, E., "Tailoring the Particle Size of Monodispersed Colloidal Gold." *Colloids and Surfaces*, Jan. 1999, 146(1-3):139-152, doi: 10.1016/S0927-7757(98)00790-0.

Gupta, A.K., Gupta, M., "Synthesis and Surface Engineering of Iron Oxide Nanoparticles for Biomedical Applications." *Biomaterials*, Jun. 2005, 26(18):3995-4021, doi: 10.1016/j.biomaterials.2004.10.012.

Huang, R-Y et al., "Redox-Sensitive Polymer/SPIO Nanocomplexes for Efficient Magnetofection and MR Imaging of Human Cancer Cells." *Langmuir*, May 2015, 31:6523-6531, doi: 10.1021/acs.langmuir.5b01208.

Jayant, R.D. et al, "Sustained-Release nanoART Formulation for the Treatment of NeuroAIDS." *Int. J. Nano.*, Feb. 2015, 10:1077-1093, doi: 10.2147/IJN.S76517.

Ji, X. et al., "Size Control of Gold Nanocrystals in Citrate Reduction: The Third Role of Citrate." *J. Am. Chem. Soc.*, Jun. 2007, 129:13939-13948, doi: 10.1021/ja074447k.

Jing, L. et al., "Prussian Blue Coated Gold Nanoparticles for Simultaneous Photoacoustic/CT Bimodal Imaging and Photothermal Ablation of Cancer." *Biomaterials*, Apr. 2014, 35:5814-5821, doi: 10.1016/j.biomaterials.2014.04.005.

Kami, D. et al., "Pleiotropic Functions of Magnetic Nanoparticles for ex vivo Gene Transfer." *Nanomedicine*, Mar. 2014, 10:1165-1174, doi: 10.1016/j.nano.2014.03.018.

Kaushik, A. et al., "Investigation of Ac-Magnetic Field Stimulated Nanoelectroporation of Magneto-Electric Nano-Drug-Carrier Inside CNS Cells." *Sci. Rep.*, Apr. 2017, 7(45663):1-12, doi: 10.1038/srep45663.

Kaushik, A. et al., "Magnetically Guided Central Nervous System Delivery and Toxicity Evaluation of Magneto-Electric Nanocarriers." *Sci. Rep.*, May 2016, 6(25309):1-10, doi: 10.1038/srep25309.

Kaushik, A. et al, "The Potential of Magneto-Electric Nanocarriers for Drug Delivery." *Expert Opin. Drug Deliv.*, Oct. 2014, 11(10):1635-1646, doi: 10.1517/17425247.2014.933803.

Kennedy, L.C. et al., "A New Era for Cancer Treatment: Gold-Nanoparticle-Mediated Thermal Therapies." *Small*, Jan. 2011, 7(2):169-183, doi: 10.1002/smll.201000134.

Lee, N. et al., "Nano-Sized CT Contrast Agents." *Adv. Mater*, Apr. 2013, 25(19):2641-2660, doi: 10.1002/adma.201300081.

Li, Y. et al., "Biocompatibility of $Fe_3O_4$@Au Composite Magnetic Nanoparticles In Vitro and In Vivo." *Int. J. Nano.*, Nov. 2011, 6:2805-2819, doi: 10.2147/IJN.S24596.

Li, Y. et al., "Gold Nanoparticle-Based Biosensors." *Gold Bulletin*, Mar. 2010, 43(1):29-41, doi: 10.1007/BF03214964.

Lin, J. et al., "Gold-Coated Iron (Fe@Au) Nanoparticles: Synthesis, Characterization, and Magnetic Field-Induced Self-Assembly." *Journal of Solid State Chemistry*, Jun. 2001, 159(1):26-31, doi: 10.1006/jssc.2001.9117.

Lyon, J.L. et al., "Synthesis of Fe Oxide Core/Au Shell Nanoparticles by Iterative Hydroxylamine Seeding." *Nano Letters.*, Feb. 2004, 4(4):719-723, doi: 10.1021/nl035253f.

Mandal, M. et al., "Magnetite Nanoparticles with Tunable Gold or Silver Shell." *Journal of Colloid and Interface Science*, Feb. 2005, 286:187-194, doi: 10.1016/j.jcis.2005.01.013.

Mohammad, F. et al., "Influence of Gold Nanoshell on Hyperthermia of Superparamagnetic Iron Oxide Nanoparticles." *J. Phys. Chem.*, Sep. 2010, 114:19194-19201, doi: 10.1021/jp105807r.

Nair, M. et al., "Getting Into the Brain: Potential of Nanotechnology in the Management of NeuroAIDS." *Advanced Drug Delivery Reviews*, Mar. 2016, 103:202-217, doi: 10.1016/j.addr.2016.02.008.

Nam, J. et al., "pH-Induced Aggregation of Gold Nanoparticles for Photothermal Cancer Therapy." *J. Am. Chem. Soc.*, Mar. 2009, 131:13639-13645, doi: 10.1021/ja902062j.

Narayanan, S. et al., "Biocompatible Magnetite/Gold Nanohybrid Contrast Agents via Green Chemistry for MRI and CT Bioimaging." *ACS Appl. Mater. Interfaces*, Nov. 2011, 4(1): 251-260, doi: 10.1021/am201311c.

Ohtsuki, S., Terasaki, T., "Contribution of Carrier-Mediated Transport Systems to the Blood-Brain Barrier as a Supporting and Protecting Interface for the Brain; Importance for CNS Drug Discovery and Development." *Pharmaceutical Research*, Sep. 2007, 24(9):1745-1758, doi: 10.1007/s11095-007-9374-5.

Pankhurst, Q.A. et al., "Applications of Magnetic Nanoparticles in Biomedicine." *J. Phys. D: Appl. Phys.*, Jun. 2003, 36:167-181.

Pham, T.T.H. et al., "Application of Citrate-Stabilized Gold-Coated Ferric Oxide Composite Nanoparticles for Biological Separations." *Journal of Magnetism and Magnetic Materials*, Mar. 2008, 320:2049-2055, doi: 10.1016/j.jmmm.2008.03.0150.

Raymond, A.D. et al., "Microglia-Derived HIV Nef+ Exosome Impairment of the Blood-Brain Barrier is Treatable by Nanomedicine-Based Delivery of Nef Peptides." *J. Neurovirol.*, Apr. 2016, 22(2):129-139, doi: 10.1007/s13365-015-0397-0.

Ren, J. et al., "Facile Synthesis of Superparamagnetic $Fe_3O_4$@Au Nanoparticles for Photothermal Destruction of Cancer Cells." *Chem. Commun.*, Sep. 2011, 47:11692-11694, doi: 10.1039/c1cc15528h.

Rosensweig, R.E., "Heating Magnetic Fluid With Alternating Magnetic Field." *Journal of Magnetism and Magnetic Materials*, Nov. 2002, 252:370-374, doi: 10.1016/S0304-8853(02)00706-0.

Salado, J. et al., "Functionalized $Fe_3O_4$@Au Superparamagnetic Nanoparticles: In Vitro Bioactivity." *Nanotechnology*, Jul. 2012, 23(315102):1-10, doi: 10.1088/0957-4484/23/31/315102.

Sayed, F.N., Polshettiwar, V., "Facile and Sustainable Synthesis of Shaped Iron Oxide Nanoparticles: Effect of Iron Precursor Salts on the Shapes of Iron Oxides." *Sci. Rep.*, May 2015, 5(9733):1-14, doi: 10.1038/srep09733.

Tassa, C. et al., "Dextran-Coated Iron Oxide Nanoparticles: A Versatile Platform for Targeted Molecular Imaging, Molecular Diagnostics and Therapy." *Acc. Chem. Res.*, Oct. 2011, 44(10):842-852, doi: 10.1021/ar200084x.

Tomitaka, A. et al., "Magnetic Characterization of Surface-Coated Magnetic Nanoparticles for Biomedical Application." *Journal of Magnetism and Magnetic Materials*, May 2011, 323(10):1398-1403, doi: 10.1016/j.jmmm.2010.11.054.

Tomitaka, A. et al., "Magnetic Nanoparticle Hyperthermia Using Pluronic-Coated $Fe_3O_4$ Nanoparticles: An In Vitro Study." *J. Nano.*, Mar. 2012, 2012(480626):1-5, doi: 10.1155/2012/480626.

Tomitaka, A. et al., "Preparation of Biodegradable Iron Oxide Nanoparticles with Gelatin for Magnetic Resonance Imaging." *Inflammation and Regeneration*, Jan. 2014, 34(1):45-55doi: 10.2492/inflammregen.34.045.

Tong, S. et al., "Coating Optimization of Superparamagnetic Iron Oxide Nanoparticles for High $T_2$ Relaxivity." *Nano Lett.*, Nov. 2010, 10(11):4607-4613, doi: 10.1021/nl102623x.

Wang, L.V., Song H., "Photoacoustic Tomography: In Vivo Imaging from Organelles to Organs." *Science*, Mar. 2012, 335(6075):1458-1462, doi: 10.1126/science.1216210.

Wilczewska, A.Z. et al., "Nanoparticles as Drug Delivery Systems." *Pharmacological Reports*, Sep.-Oct. 2012, 64(5):1020-1037, doi: 10.1016/S1734-1140(12)70901-5.

Wilhelm, I. et al., "In Vitro Models of the Blood-Brain Barrier." *Acta Neurobiol. Exp.*, Jan. 2011, 71:113-128.

Wohlfart, S. etal., "Transport of Drugs Across the Blood-Brain Barrier by Nanoparticles." *Journal of Controlled Release*, Jul. 2012, 161(2):264-273, doi: 10.1016/j.jconrel.2011.08.017.

Xing, H. et al., "Multifunctional Nanoprobes for Upconversion Fluorescence, MR and CT Trimodal Imaging." *Biomaterials*, Feb. 2012, 33(4):1079-1089, doi: 10.1016/j.biomaterials.2011.10.039.

(56) References Cited

OTHER PUBLICATIONS

Xing, Y. et al., "Controllable Synthesis and Characterization of $Fe_3O_4$/Au Composite Nanoparticles." *Journal of Magnetism and Magnetic Materials*, Apr. 2015, 380:150-156, doi: 10.1016/j.jmmm.2014.09.060.

Xu, C. et al., "Size and Concentration Effect of Gold Nanoparticles on X-Ray Attenuation as Measured on Computed Tomography." *Chem. Mater.*, Jul. 2008, 20(13):4167-4169, doi: 10.1021/cm8008418.

Xu, Z. et al., "Magnetic Core/Shell $Fe_3O_4$/Au and $Fe_3O_4$/Au/Ag Nanoparticles with Tunable Plasmonic Properties." *J. Am. Chem. Soc.*, May 2007, 129:8698-8699, doi: 10.1021/ja073057v.

Yang, H. et al., "Targeted Dual-Contrast $T_1$- and $T_2$-Weighted Magnetic Resonance Imaging of Tumors Using Multifunctional Gadolinium-Labeled Superparamagnetic Iron Oxide Nanoparticles." *Biomaterials*, Mar. 2011, 32:4584-4593, doi: 10.1016/j.biomaterials.2011.03.018.

Yavuz, C.T. et al., "Low-Field Magnetic Separation of Monodisperse $Fe_3O_4$ Nanocrystals." *Science*, Nov. 2006, 314(5801):964-967, doi: 10.1126/science.1131475.

Zeng, S. et al., "A Review on Functionalized Gold Nanoparticles for Biosensing Applications." *Plasmonics*, Apr. 2011, 6:491-506, doi: 10.1007/s11468-011-9228-1.

Zlokovic, B.V., "The Blood-Brain Barrier in Health and Chronic Neurodegenerative Disorders." *Neuron*, Jan. 2008, 57(2):178-201, doi: 10.1016/j.neuron.2008.01.003.

Tomitaka, A., et al., "Development of magneto-plasmonic nanoparticles for multimodal image-guided therapy to the brain." Nanoscale, Jan. 2017, 9(2): 764-773.

\* cited by examiner

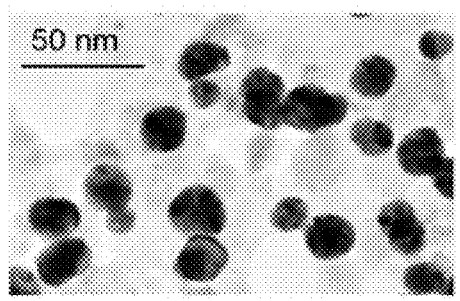
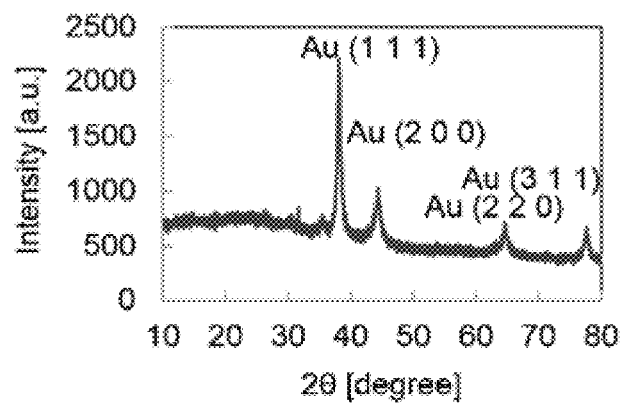
FIG. 2A
FIG. 2B
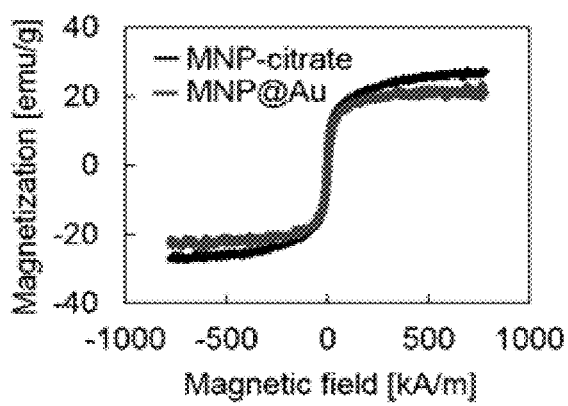
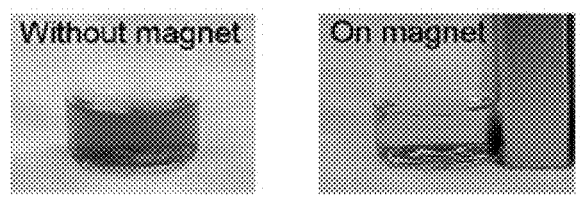
FIG. 2C
FIG. 2D
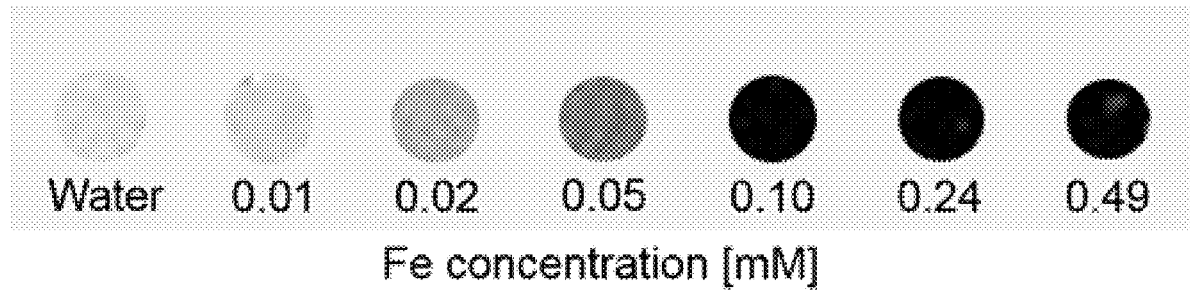
FIG. 3A

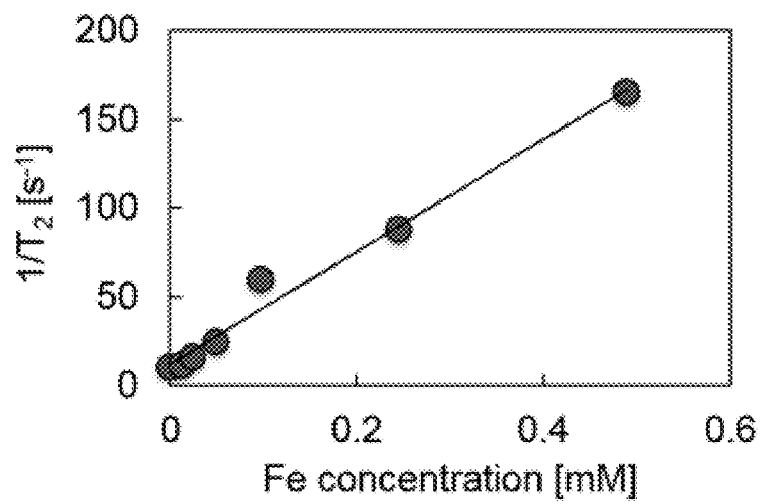
FIG. 3B
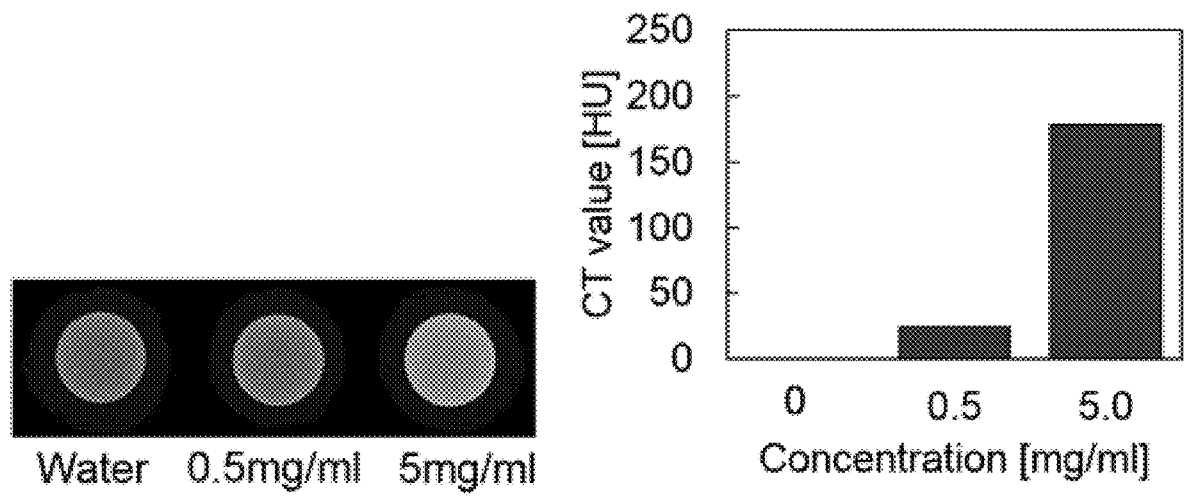
FIG. 3C
FIG. 3D

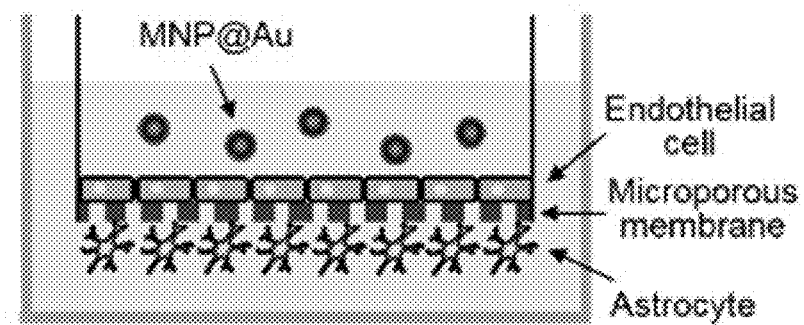
FIG. 5A
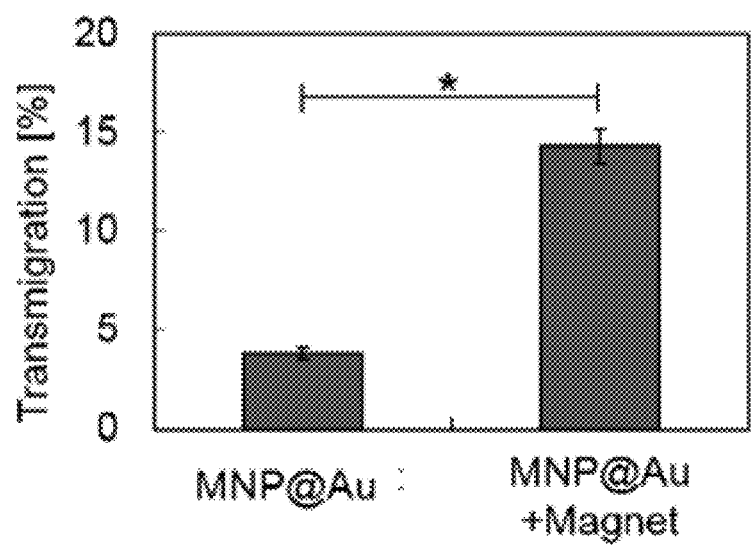
FIG. 5B
| | Control | MNP@Au | MNP@Au +Magnet |
|---|---|---|---|
| TEER Ω/cm² | 195.5 ± 13.0 | 194.2 ± 5.2 | 197.7 ± 4.7 |
FIG. 5C MNP@Au:
Iron oxide core + Au shell 33.0 nm, δ 4.4

Magneto-gold nanostar:
Iron oxide core + Au nanostar shell 72.5 nm, δ 14.3

STIMULI-RESPONSIVE MAGNETO-PLASMONIC NANOCARRIER

GOVERNMENT SUPPORT

This invention was made with government support under DA037838, DA040537, and DA034547 awarded by The National Institutes of Health. The government has certain rights in the invention.

BACKGROUND OF THE INVENTION

Nanomedicine, which is based on administration of nanomaterials to prevent, diagnose, and/or treat diseases, has attracted attention for a few decades. Recent progress in nanotechnology facilitated biomedical applications of nanomaterials such as, drug carriers.

Currently-available nanocarriers are capable of releasing therapeutic agents when subjected to external stimulation following targeted delivery to a treatment area of interest. However, many of these existing nanocarriers, in addition to requiring complexed formulation, are not applicable to a number of regions that are particularly sensitive to external stimuli such as, for example, heat. Furthermore, regions such as the brain possess cellular tight junctions that could limit the transmigration of nanocarriers to the targeted treatment area. As a result, there remains a need for nanocarriers that can be delivered in a targeted manner while accommodating various drug release mechanisms.

BRIEF SUMMARY OF THE INVENTION

The subject invention provides materials and methods for synthesizing nanoparticles, particularly, magneto-plasmonic nanoparticles, and methods for using the magneto-plasmonic nanoparticles in therapeutic, diagnostic (theranostic) applications.

In one embodiment, the invention provides a method for synthesizing magnetic core/gold shell nanoparticles (MNP@Au) and magneto-plasmonic gold nanostars by a seeding method. In a particular embodiment, the seeding method comprises using iron oxide nanoparticles as seeds and reducing $Au^{3+}$ using a reducing agent such as, for example, sodium citrate, ascorbic acid, sodium borohydride, and polyvinyl pyrrolidine.

Certain embodiments of the invention provide a formulation comprising MNP@Au bound to or co-loaded with a therapeutic agent. The MNP@Au bound to or co-loaded with the therapeutic agent can be encapsulated within liposomes.

MNP@Au synthesized with the method described herein have hydrodynamic size and optical properties advantageous for theranostic applications, particularly, for transport of magneto-plasmonic nanoparticles through the BBB.

One embodiment of the invention provides a formulation comprising MNP@Au bound to, or co-loaded with, a therapeutic agent. In an exemplary embodiment, the therapeutic agent treats a brain disease. In one embodiment, liposomes comprising MNP@Au bound to or co-loaded with a therapeutic agent are surface-modified with an affinity ligand that targets the liposomes to a target tissue, such as the brain.

A further embodiment of the invention provides a method for treating a brain disease in a subject, the method comprising administering to the subject a formulation comprising MNP@Au bound to, or co-loaded with, a therapeutic agent and applying to the subject magnetic forces to guide the MNP@Au across the BBB and into brain parenchyma.

The therapeutic agent can be released into the brain parenchyma by applying an alternating current (AC) magnetic field and/or a near-infrared light (NIR) to the subject, the required energy source depending upon the nature of the nanoparticles.

A further embodiment of the invention provides a method for imaging a target site in a subject, the method comprising administering to the subject MNP@Au, optionally conjugated to, or mixed with, a therapeutic agent and, optionally, further encapsulated within liposomes, applying a magnetic field to the subject to facilitate transport of MNP@Au to the target site, and applying to the subject a magnetic field, x-rays, and/or non-ionizing radiation (e.g., visible, NIR, and UV light) to visualize MNP@Au in the target site.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-2D. TEM image of MNP@Au (2A), X-ray diffraction (XRD) patterns of MNP@Au (2B), magnetization curves of MNP-citrate and MNP@Au (2C), and picture of MNP@Au attracted by magnet (2D). The average diameter of MNP@Au was 14.5 nm. MNP@Au showed superparamagnetic property and Au specific diffraction pattern.

FIGS. 3A-3D. $T_2$-weighted MRI images (3A), transverse relaxivity (3B), micro-CT images (3C; CT: X-ray computed tomography), and CT values (3D) of MNP@Au. Magnetic resonance imaging (MRI) results showed strong negative contrast in a Fe concentration dependent manner, and linear correlation between transverse relaxivity and Fe concentration was observed. Micro-CT images showed concentration dependent positive contrast and increase of CT values with nanoparticle concentration.

FIGS. 5A-5D. (5A) Schematic illustration of in vitro blood brain barrier (BBB) model, (5B) transmigration of PEG coated MNP@Au across an in vitro BBB model, (5C) transendothelial electrical resistance (TEER) values of the in vitro BBB model after exposure to PEG coated MNP@Au, and (5D) effect of PEG coated MNP@Au exposure on fluorescein isothiocyanate-dextran transfer in the BBB model. (*p<0.05; N=3).

DETAILED DESCRIPTION OF THE INVENTION

Figure 1A:
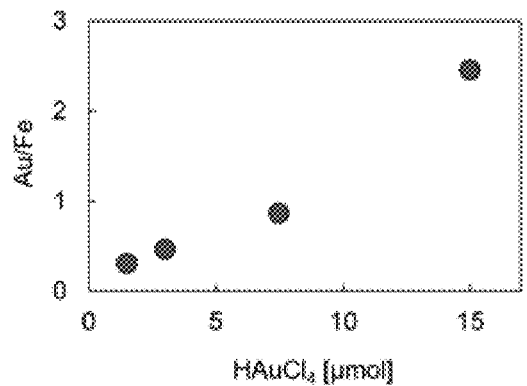
FIGS. 1A-1F. Au-to-Fe weight ratio (1A), absorbance (1B), and hydrodynamic sizes (1C) of MNP-citrate and MNP@Au synthesized with initial $HAuCl_4$ varied from 1.5 to 15 µmol and fixed concentration of sodium citrate (5 mM). Au-to-Fe weight ratio (1D), absorbance (1E), and hydrodynamic sizes (1F) of MNP@Au synthesized with initial $HAuCl_4$ of 15 mol and sodium citrate concentrations varied from 0.5 to 20 mM. All the samples for UV-vis and hydrodynamic size measurements were prepared at Fe concentration of 10 µg/ml. Inset: Absorbance of MNP@Au synthesized with 0.5 and 5 mM sodium citrate per unit mass of Au, and pictures MNP@Au samples.

Magnetic nanoparticles react with an external magnetic field and show unique properties based on the condition of the magnetic field. A magnetic field gradient exerts magnetic force on magnetic nanoparticles, depending on physical parameters such as particle volume, susceptibility of particles, and a field gradient. The magnetic force improves the delivery to a specific location of a therapeutic agent conjugated or mixed with magnetic nanoparticles. When an alternating magnetic field is applied, magnetic nanoparticles induce heat based on hysteresis loss and relaxation losses. The temperature rise from magnetic nanoparticles can be controlled by changing the strength and frequency of an alternating magnetic field. Due to these unique properties, magnetic nanoparticles have been applied for various biomedical applications, including magnetic resonance imaging (MRI), drug delivery, gene transfection, and hyperthermia (heat treatment).

Iron oxide nanoparticles ($Fe_3O_4$ and $\gamma$-$Fe_2O_3$) are the most commonly used magnetic nanoparticles for biomedical applications due to their biocompatibility. Coating the iron oxide nanoparticles with various materials such as dextran, polymers, and silica helps functionalize the surface of the nanoparticles and avoid aggregation. These surface-modified and functionalized magnetic nanoparticles can be used as nanocarriers for drug delivery to the brain and imaging probes for brain diseases. In addition, enhanced transmigration of magnetic nanoparticles and magneto-electric nanoparticles using magnetic targeting is reported.

Gold (Au) has been used for numerous medical applications because of its biocompatibility, in vivo stability, and versatility in surface functionalization. In addition to these properties, Au nanoparticles change color with their size and shape due to surface plasmon resonance (SPR). When the wavelength of light is much larger than the nanoparticle size and has resonance frequency, it causes polarization of the free-electrons in the metal to one surface and oscillations in resonance with the light's frequency. The resonance frequency depends on particle size, shape, dielectric properties, aggregate morphology, surface modification, and surrounding medium. The shift of resonance frequency caused by those factors makes gold nanoparticles strong candidates for biosensors. This unique optical property makes gold nanoparticles particularly valuable for imaging, including photoacoustic imaging. Gold nanoparticles also possess great X-ray attenuation, which makes them attractive contrast agent for X-ray computed tomography (CT). The strong absorption of light due to SPR is also converted into heat, which makes gold nanoparticles a good heat sources for hyperthermia. The combination of magnetic material and gold within the nanoscale system gives multi-functionalities that enable theranostic applications, multi-modal imaging, and multi-modal image-guided therapies. These strategies allow more efficient treatment with precise targeting and tracking of treatment progress.

Several synthesis methods have been reported for MNP@Au, such as the microemulsion method, iterative hydroxylamine seeding process, and seeded growth using citrate reduction.

In one embodiment, the invention provides a method for synthesizing MNP@Au magneto-plasmonic nanoparticles. MNP@Au synthesized with the method described herein has hydrodynamic size and optical properties of MNP@Au that are optimal for theranostic applications, particularly, for transmigration of magneto-plasmonic nanoparticles through BBB.

In certain embodiments, a method for synthesizing MNP@Au magneto-plasmonic nanoparticles comprises using iron oxide nanoparticles as seeds and reducing $Au^{3+}$ using a reducing agent, for example, sodium citrate. In one embodiment, the method for synthesizing MNP@Au magneto-plasmonic nanoparticles comprises the steps of:

a) contacting magnetic nanoparticles with an acid and optionally, sonicating the resultant mixture;

b) adding citrate reducing agent to the mixture produced in step a) and optionally, sonicating the resultant mixture to produce modified magnetic nanoparticles;

c) washing and separating the modified nanoparticles from the mixture produced in step b);

d) dispersing and sonicating the modified nanoparticles produced in step c) in another solution of the reducing agent and heating the resultant mixture to boiling temperature, optionally, with stirring; and e) adding a gold precursor to the mixture produced in step d) to produce nanoparticles with a magnetic core and a gold shell.

The MNP@Au can then be isolated from solution using, for example, magnetic force, and washed with distilled water to remove any impurities or other chemicals that may not have been removed during the washing steps. Accordingly, one embodiment of the invention provides MNP@Au produced according to the method comprising steps a) to e) described above.

In further embodiments, the subject invention provides methods for synthesizing magneto-plasmonic gold nanostars from the MNP@Au provided herein, the method of synthesis including the steps of:

a) dispersing MNP@Au in a solution comprising a gold precursor;

b) adding $AgNO_3$ to the solution of step a);

c) adding an acid to the mixture of step b); and d) neutralizing the solution with a base.

The resulting magneto-plasmonic nanostars can then be isolated using magnetic force and redispersed in distilled water.

In some embodiments, the acid can be any acid capable of reducing the pH of a solution including, but not limited to, hydrochloric acid, acetic acid, and sulfuric acid. An exemplary embodiment provides that the acid is hydrochloric acid (HCl). In some embodiments, the base can be any base capable of increasing the pH of a solution and can be, for example, a strong base such as sodium hydroxide. In some embodiments, the reducing agent can be, for example, sodium citrate, ascorbic acid, sodium borohydride, or polyvinyl pyrrolidine.

In one embodiment, in step a), HCl at a concentration between 1.5 M to 2.5 M, preferably, between 1.75 M to 2.25 M, and even more preferably at about 2 M, is contacted with about 1 mg/ml to 3 mg/ml or about 2 mg/ml of magnetic nanoparticles and sonicated, for example, in a bath sonicator, for about 20 mins to 40 mins, preferably, between 25 minutes to 35 minutes, and even more preferably, about 30 minutes.

In one embodiment, one volume of the solution produced in step a) is mixed with about one volume of sodium citrate at a concentration between 15 mg/ml to 25 mg/ml and preferably, about 20 mg/ml. This mixture is sonicated for about 15 minutes to 25 minutes, and preferably, for about 20 min using bath sonication, followed by about 5 to 10 minutes of probe sonication using about 15% to 25%, and preferably, about 20% amplitude.

In one embodiment, citrate coated magnetic nanoparticles are washed with distilled water to remove impurities and other ingredients from the citrate coated magnetic nanoparticles. Such washing can be done by sonication and centrifugation. A preparation of citrate coated magnetic nanoparticles is produced at the end of this step.

In a further embodiment, citrate coated magnetic nanoparticles produced as described above are mixed at a concentration of between 0.025 mM to 0.075 mM, and preferably, 0.05 mM, in a solution of sodium citrate and sonicated for about 5 to 10 minutes at about 20% amplitude prior to heating at boiling temperature with stirring between 250 to 350 rpm, preferably at 300 rpm. To this mixture, a gold precursor is added and stirred. As provided herein, a gold precursor can be, for example, $HAuCl_4$, $AuCl_3$, or $Au(OH)_3$. In one embodiment, the step of coating the MNP citrate nanoparticles with Au can be carried out with the initial $HAuCl_4$ concentration between 1.5 to 15 μmol and about 5 mM sodium citrate. In another embodiment, 15 μmol of $HAuCl_4$ is used with varying concentration of sodium citrate between 0.5 mM to 20 mM.

MNP@Au produced in the previous step can be isolated using a magnetic field and washed to remove further impurities and other ingredients used in its preparation.

MNP@Au produced as described herein can be further modified and/or formulated. In one embodiment, the MNP@Au are bound to or co-loaded with a therapeutic agent and encapsulated within liposomes. In certain embodiments, MNP@Au bound to a therapeutic agent are encapsulated within liposomes, which results in the formation of a therapeutic agent-loaded magneto-plasmonic liposome. In certain embodiments, the liposomes provide biocompatibility for MNP@Au, allowing the therapeutic agent to pass the BBB in response to an external magnetic field. The therapeutic agent-loaded magnetic liposomes can be further surface-modified with specific affinity ligands, such as polyclonal/monoclonal antibodies, peptides, peptidomimetics, specific physiological ligands/analogues that target the MNP@Au-containing liposomes applicable to various target treatment areas including, for example, the brain.

The liposomes can be formed by methods described herein. In some embodiments, liposomes provided herein comprise a mixture of lipids and cholesterol. In some embodiments, the liposomes comprise only lipids. The liposomes optionally can further be formed with dihexadecyl phosphate (DHDP) and distearoyl phosphatidyl ethanolamine (DSPE). The liposomes can include polyethylene glycol moieties. For example, the liposomes can be prepared using a phosphatidyl moiety further having a polyethylene glycol (PEG) moiety. The PEG moiety, if present, extends from the surface of the liposome into the surrounding environment. The presence of a PEG moiety stabilizes the circulating half-life of the liposomes and further provides a sustained release type formulation for the therapeutic agents bound to the magnetic nanoparticles in the liposomes.

In one embodiment, MNP@Au and magneto-plasmonic nanostar have a coating, preferably, a biocompatible coating. Suitable coatings include thiol-containing molecules such as, for example, thiol PEG (e.g., PEG-SH, HS-PEG-COOH, $HS-PEG-NH_2$), 11-Mercaptoundecanoic acid, and thiol-containing peptides.

In another embodiment, MNP@Au and magneto-plasmonic nanostars have, respectively, a citrate acid and ascorbic acid on their surface, which allows for ionic binding of a therapeutic agent thereto. This binding can be reversible and allows for the bound therapeutic agent to be released at a target site. The amount of therapeutic agent bound to the MNP@Au or the nanostars can be controlled by the molar ratio of therapeutic agent to the nanoparticles, incubation time for mixing of the two components, the pH of the incubation, the temperature of the incubation, and/or the buffers used during the incubation. For example, phosphates interact strongly with iron oxide particles, and therefore, the presence of phosphates during incubation would impact the amount of therapeutic agent bound to the nanoparticles' surface.

The therapeutic agents can be bound to the surface of the MNP@Au and magneto-plasmonic nanostars through a variety of means, including, for example, electrostatic interaction, gold-sulfur bond, metal-phosphate bond, and a combination thereof.

The subject invention provides pharmaceutical compositions comprising a therapeutically effective amount of MNP@Au and, optionally, one or more pharmaceutically acceptable carriers. Such pharmaceutically acceptable carriers can be liquids, such as water. The therapeutic composition can also comprise excipients, adjuvants, flavoring agents, etc. that facilitate processing of the active compounds into preparations that can be used pharmaceutically. Proper formulation is dependent upon the route of administration chosen. In one embodiment, the pharmaceutical composition and all ingredients contained therein are sterile.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the MNP@Au formulation, together with a suitable amount of carrier so as to provide the form for proper administration to the patient.

In one embodiment, the administration of the composition can be systemic. Oral, intravenous, intra-arterial, subcutaneous, intra-peritoneal, intra-thecal, intra-muscular, intra-ventricular, intra-nasal, transmucosal, subcutaneous, topical, rectal, and other modes of administration are all contemplated. The compositions can be designed to facilitate the subject compositions to crossing BBB.

In one embodiment, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the composition can be delivered in the form of an aerosol spray presentation from pressurized packs or a nebulizer, with the use of a suitable propellant. The composition can also be administered via inhalation or other route as a powder. In particular embodiments, the therapeutic composition is a sustained-release system. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transderinal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(-)-3-hydroxybutyric acid (EP 133,988).

In one embodiment, implantable drug infusion devices may be used to provide patients with a constant and long-term dose or infusion of a therapeutic composition. Such device can be categorized as either active or passive.

In one embodiment, polymers can be used for ion-controlled release. Various degradable and non-degradable polymeric matrices for use in controlled drug delivery are known in the art (Langer, Accounts Chem. Res. 26:537, 1993). For example, the block copolymer, poloxamer 407, hydroxyapatite, and liposomes.

The pharmaceutical composition of the present invention may be used either alone or in combination with one or more other therapeutic agents. The compositions can also be formulated in combination with at least one other agent, such as stabilizing or buffer compounds, which can be administered in any sterile, biocompatible pharmaceutical carrier, including, but not limited to, saline, buffered saline, dextrose, and water. In addition to MNP@Au and the therapeutic agent, the compositions can contain suitable pharmaceutically acceptable carriers comprising excipients and auxiliaries that facilitate processing of the active compounds into preparations that can be used pharmaceutically. The composition may be prepared as a single-dose form using a pharmaceutically acceptable carrier or excipient or may be contained in a multiple-dose container.

The compositions described herein can be used to deliver drugs to a subject in a controlled release fashion by administering to the subject the MNP@Au bound to or co-loaded with a therapeutic agent. In an embodiment, MNP@Au form ionic bonds with therapeutic cargo and applying an alternating current (AC) magnetic field to the MNP@Au weaken the attraction and release the cargo. In a further embodiment, either an AC magnetic field or a near-infrared (NIR) light can be used to release the cargo bound to a magneto-plasmonic nanostar.

In one embodiment, MNP@Au in the formulations described herein contain (i) a coating on at least a portion of the MNP@Au surface, said coating one or more of glycerol monooleate, poly L-lysine and polyethylene glycol, and (ii) a therapeutic cargo conjugated with the MNP@Au through an ionic bond.

In certain embodiments, a composition described herein is administered to a subject and the active ingredients are guided by magnetic force across the BBB into brain parenchyma and released on demand, for example, by alternating current. Accordingly, an embodiment of the invention provides a method of treating a brain disease in a subject by administering to the subject a formulation comprising MNP@Au conjugated to a therapeutic agent. The method further comprises applying an alternating current magnetic field to the subject to induce local electric charge oscillation by eddy current flow on the gold shell of the MNP@Au, or alternatively, applying an NIR light that introduces heat locally to the magneto-plasmonic nanostar, to induce release of the therapeutic agent.

The description of various aspects of MNP@Au and therapeutic agents discussed above in connection with the formulations of the invention are also applicable to the methods of treating a brain disease described herein.

Applying an AC magnetic field that equivalently sweeps all bond orientations can create a more uniform bond-breaking process over the surface of the MNP@Au and thus enhance the drug release efficacy. This can be achieved by using a spatially rotating field where the field profile is changing in time as well as in space. The field rotation in space can be accomplished, for example, by using an array of coils that generate alternating current fields with non-zero phase shifts with respect to each other, as illustrated in FIG. 2c of US20150283368. Certain aspects of the step of administering alternating current to the subject to cause the release of therapeutic cargo are described in US20150283368, for example, in paragraphs [0040] to [0056].

In other embodiments, a composition described herein is administered to a subject and the MNP@Au particles are guided by magnetic force to a target site and the MNP@Au are visualized by administering to the target site one or more of a magnetic field, x-rays, non-ionizing laser pulses, or light in a laser in the visible, near infrared, or near ultraviolet range.

To facilitate this embodiment, the subject invention provides methods for synthesizing and using magneto-plasmonic nanoparticles, particularly, MNP@Au, which have a magnetic core and gold shell structure. The methods of synthesizing comprise reduction of Au ions on magnetic nanoparticle using, for example, sodium citrate. The hydrodynamic sizes and optical properties of magneto-plasmonic nanoparticles varied with changing Au ion and sodium citrate concentrations.

The synthesized magneto-plasmonic nanoparticles exhibit superparamagnetic property, and $T_2$-weighted MRI and X-ray CT imaging contrasts in a concentration-dependent manner. The transmigration of magneto-plasmonic nanoparticles across the in vitro BBB when an external magnetic field was applied was significantly enhanced without disrupting the integrity of the BBB. Accordingly, the magneto-plasmonic nanoparticles described herein can be used for brain-targeted theranostic applications and image-guided therapies.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X+10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

"Treatment" or "treating" and grammatical variants of these terms, as used herein refer to an approach for obtaining beneficial or desired results including but not limited to therapeutic benefit. A therapeutic benefit is achieved with the eradication or amelioration of one or more of the physiological symptoms associated with one or more diseases within the scope of the subject invention such that an improvement is observed in the patient, notwithstanding that the patient may still be afflicted with the one or more diseases.

All patents, patent applications, provisional applications, and publications referred to or cited herein are incorporated by reference in their entirety, including all figures and tables, to the extent they are not inconsistent with the explicit teachings of this specification.

Materials and Methods

Materials

Iron(III) chloride (reagent grade, 97%), hydrochloric acid (36.5-38.0%, BioReagent, for molecular biology), sodium sulfite (BioUltra, anhydrous, ≥98% (RT)), ammonium hydroxide (28% NH3 in H2O, ≥99.99% trace metals basis), sodium citrate dihydrate (≥99%, FG), Gold(III) chloride trihydrate (ACS reagent, ≥49.0% Au basis), potassium thiocyanate (ACS reagent, ≥99.0%), XTT sodium salt (BioReagent), phenazine methosulfate, Fibronectin from bovine plasma, and Fluorescein isothiocyanate-dextran (molecular weight 40,000 Da) were purchased from Sigma-Aldrich. Ultra Pure Agarose was purchased from Invitrogen. mPEG-Thiol, Mw 5000 was purchased from Laysan Bio, Inc. Human brain astrocytes (HAs), human brain endothelial cells (HBMECs), their culture medium, and poly-L-lysine were purchased from ScienCell Research Laboratories.

Synthesis of Magnetic Nanoparticles

Magnetic nanoparticles (MNPs) were synthesized by a co-precipitation method. Briefly, Iron(III) chloride hexahydrate ($FeCl_3.6H_2O$, 1.17 g) dissolved in water and Iron(II) chloride tetrahydrate ($FeCl_2.4H_2O$, 0.43 g) dissolved in 2M hydrochloric acid solution were mixed. The temperature of the solution was increased to 70° C. and ammonium hydroxide was added dropwise with stirring at 200 rpm. Immediately after addition of ammonium hydroxide, the color of the solution turned black. After 30 min of stirring, an aqueous solution containing 0.95 g of sodium citrate was added and the temperature of the solution was further increased to 90° C. This reaction was continued for 30 min under stirring at 400 rpm. The synthesized citrated-coated MNPs (MNP-citrate) were purified with water by using a centrifuge followed by 30 min of sonication.

Synthesis of MNP@Au Magneto-Plasmonic Nanoparticles

MNP@Au magneto-plasmonic nanoparticles were synthesized by the method previously reported by our group with slight modification. Briefly, MNP-citrate (0.05 mM) dispersed in 5 mM sodium citrate was sonicated using probe sonicator at 20% amplitude prior to gold coating. This solution was heated to boiling temperature and $HAuCl_4$ was added under stirring at 300 rpm. After 6 min reaction, the resulting nanoparticles (core-shell nanoparticles of magnetic nanoparticles core and Au shell) MNP@Au were collected using magnet and redispersed into distilled water.

Synthesis of Magneto-Plasmonic Nanostars

MNP@Au (0.36 mg) was dispersed in 40 ml of 0.21 mM $HAuCl_4$ aqueous solution. Silver nitrate was added to the solution under stirring at 400 rpm. Immediately after the addition of $AgNO_3$ (2.4 μmol), 800 μl of 100 mM L-Ascorbic acid was added to the mixture and followed by 1 min of stirring at room temperature. After 1 min of reaction, 1M sodium hydroxide solution was added to neutralize the reaction mixture. The resulting magneto-plasmonic nanostars were collected using a magnet and redispersed into distilled water.

Characterization of MNP@Au Magneto-Plasmonic Nanoparticles

The iron and gold concentrations were determined using an inductively coupled plasma mass spectrometer (ICP-MS, Perkin Elmer Sciex, model ELAN DRC-II). Samples were dissolved in aqua regia and diluted by deionized water prior to the measurement. Optical properties of MNP@Au were determined by measuring absorbance using a UV-Visible Spectrophotometer (HITACHI U-2910). Samples were diluted with distilled water to the Fe concentration of 10 μg/ml. The hydrodynamic sizes and zeta potentials of MNP@Au were measured by Zetasizer Nano-ZS (Malvern instruments). 10 μl of MNP@Au were dispersed in 1 ml distilled water. Transmission electron microscopy (TEM) images were acquired using a Phillips CM-200 200 kV transmission electron microscope operated at 80 kV. X-ray powder diffraction (XRD) pattern of MNP@Au was recorded with a Siemens D-5000 diffractometer with Cu Kα radiation (λ=0.154056 nm). The magnetization curves of MNP-citrate and MNP@Au were measured using a vibrating sample magnetometer (VSM-3, Toei Kogyo) equipped with an electromagnet (TEM-WFR7, Toei Kogyo) and a gaussmeter (Model 421, Lake Shore Cryotronics, Inc.). The measurement was conducted at room temperature with a maximum field of 780 kA/m.

Multimodal Imaging Property of MNP@Au Magneto-Plasmonic Nanoparticles

The MRI property of MNP@Au was evaluated in a 30 cm horizontal bore 7-Tesla MRI system (Bruker Biospin). An aqueous solution of nanoparticles (100 µl) was placed into a polymerization chain reaction (PCR) tube and fixed with 1 wt % agar. Sample temperature was maintained at room temperature. The transverse relaxation time ($T_2$)-weighted images were obtained with the following parameters: pulse repetition time (TR) 2000 ms, echo time (TE) 5.21 ms, slice thickness (ST) 1 mm, and number of acquisitions (NA) 12.

Micro-CT imaging was conducted using Skyscan1172 (Bruker) with a source voltage of 40 kV and a current of 250 µA. CT values were estimated in Hounsfield units (HU) by calibration with water and air as 0 HU and −1000 HU, respectively.

PEGylation of MNP@Au Magneto-Plasmonic Nanoparticles

Polyethylene glycol (PEG) has been used to improve the stability of nanoparticles and increase circulation time for in vivo applications. The optimized MNP@Au was coated with PEG to improve stability in biological buffer to allow for further cytotoxicity and in vitro BBB experiments. For the coating process, mPEG-Thiol (100 ml of 0.5 mg/ml) was added to 15 mg of MNP@Au and stirred at 300 rpm overnight. PEG-coated MNP@Au (MNP@Au-PEG) was purified three times using a centrifuge and sonicated for 1 min at 20% amplitude using a probe sonicator.

Cytotoxicity of MNP@Au and MNP@Au-PEG

The cytotoxicity of MNP@Au and MNP@Au-PEG was evaluated by XTT (Sodium 3,3'-(-[(Phenlamino)carbonyl]-3,4-tetrazolium)-bis(4-methoxyl-6-nitro)benzene sulfonic acid hydrate) assay. Primary human astrocytes were seeded in a 96-well cell culture plate at a density of $1\times10^4$ cells/well. After 24 h of incubation at 37° C., the medium was replaced with 100 µl of fresh medium containing 10-100 µg/ml of MNP@Au. After 24 and 48 hr incubation, cells were washed twice with PBS and 100 µl of fresh medium was added. The XTT/PMS mixture solution was prepared by mixing XTT and phenazine methosulfate (PMS) immediately before use. 25 µl of XTT/PMS mixture solution was added to each well and incubated at 37° C. for 4 hr. Absorbance was measured at 450 nm using a microplate reader (Synergy HT, multi-mode microplate reader, BioTek).

Experiments were performed in quadruplicate replicates (N=3). The results are represented as the mean±standard deviation. Statistical analysis was performed using one-way analysis of variance (ANOVA) followed by Tukey's multiple comparison test and difference was considered significant at $P<0.05$.

Preparation of Magneto-Plasmonic Liposomes

MNP@Au was coated with polyethylene glycol (PEG) before liposomal preparation. Briefly, mPEG-Thiol (0.5 mg/ml) was added to MNP@Au and stirred at 300 rpm overnight. PEG-coated MNP@Au (MNP@Au-PEG) was purified using centrifuge and sonicated for 1 min using probe sonicator at 20% amplitude.

Magneto-plasmonic liposomes were prepared by a hydration method. DPPC and cholesterol were mixed in chloroform and evaporated using rotary evaporator. The resulting film was hydrated with 10 mM HEPES buffer saline containing 0.2 mg/ml of MNP@Au-PEG and tenofovir and kept in a water bath at 50° C. for 2 hr. After the hydration, unilamellar liposomes were obtained by extrusion process using a membrane with pore size of 0.2 µm followed by purification using centrifuge at 1000 g. For the optimization of liposomal formulation, the molar ratio of lipid to cholesterol was varied from 1:1, 2:1, 4:1, and no cholesterol, and the drug to lipid ratio was varied from 0.1:34 to 1:34.

Characterization of Magneto-Plasmonic Liposomes

The encapsulation efficiency of drug was measured using a UV-visible spectrophotometer. The supernatant removed at purification process of magneto-plasmonic liposomes were centrifuged at 200,000 g for 60 min to separate unencapsulated drug. The drug concentration in the supernatant was measured using UV-visible spectrophotometer. The encapsulation efficiency was calculated as $$\text{Encapsulation efficiency [\%]} = (W_{Total} - W_{Supernatant})/W_{Total} \times 100$$

where $W_{Total}$ is the total amount of drug added during preparation and $W_{supernatant}$ is the amount of drug detected in supernatant. The amount of MNP@Au encapsulated into liposomes was also measured using a UV-visible spectrophotometer. The encapsulated MNP@Au was extracted by dissolving liposomes using Triton X-100. The amount of the extracted MNP@Au was measured using a UV-visible spectrometer. Hydrodynamic sizes and zeta potentials of magneto-plasmonic liposomes dispersed in PBS were measured using a Zetasizer Nano-ZS (Malvern Instruments).

In-vitro drug release from magneto-plasmonic liposomes was performed using a dialysis membrane. The magneto-plasmonic liposomes were loaded in a dialysis membrane (Micro Float-A-Lyzer, Spectrum Labs) with molecular weight cut-off of 100 kDa and immersed in PBS. The temperature of the heater was set at 40° C. and stirring rate was kept at 200 rpm. The sample was collected at each time points up to 3 days and replaced with PBS.

TEM images of magneto-plasmonic liposomes were acquired using a Phillips CM-200 200 kV transmission electron microscope operated at 80 kV.

In Vitro Blood-Brain Barrier (BBB) Model

The in vitro BBB model was developed in a bicompartmental transwell culture plate (Corning Life Sciences). The upper chamber of this plate was separated from the lower chamber by a 10 µm thick polycarbonate membrane with 3.0 µm pores. In a 24-well cell culture plate with pore density of $2\times10^6$ pores/$cm^2$ and cell growth area of 0.33 $cm^2$, $2\times10^5$ primary human brain microvascular endothelial cells (HBMECs) and human astrocytes (HAs) were grown to confluence on the upper side and the underside of the inserts, respectively. The further experiment was conducted within 6 days after seeding the cells, and establishment of the BBB integrity was confirmed by the transendothelial electrical resistance (TEER) measurement.

The transmigration study was conducted by adding 5 µg of MNP@Au-PEG magneto-plasmonic nanoparticles to the upper chamber and incubating at 37° C. for 24 h with or without magnet (magnetic field of 150 mT at the surface of culture plate) below the cell culture plate. After incubation, the media containing the nanoparticles was collected from both the upper and lower chambers and centrifuged to precipitate nanoparticles. The concentration of the nanoparticles re-dispersed in water was measured using a UV-Visible Spectrophotometer. Transmigration efficiency was calculated as Transmigration efficiency [%]=(nanoparticle concentration in lower chamber)/((nanoparticle concentration in lower chamber)+(nanoparticle concentration in upper chamber))×100.

The effect of nanoparticle exposure on the integrity of the in vitro BBB was determined by measuring TEER using Millicell ERS microelectrodes (Millipore) after exposure of the nanoparticles to the BBB model.

The effect of nanoparticle exposure to the permeability of the in vitro BBB model was determined by measuring the transfer of fluorescein isothiocyanate-dextran (FITC-dextran) through the BBB model. Briefly, 100 µg of FITC-dextran was added to the upper chamber and further incubated for 4 h. Samples were collected from the lower chamber and fluorescence was measured at an excitation wavelength of 485 nm and an emission wavelength of 520 nm using a microplate reader (Synergy HT, multi-mode microplate reader, BioTek). The permeability was calculated as a percentage of FITC-dextran transported across the BBB model compared to FITC-dextran transported across the inserts without cells. Experiments were performed in duplicate replicates (N=3). The results are represented as the mean±standard deviation.

Following are examples which illustrate procedures for practicing the invention. These examples should not be construed as limiting. All percentages are by weight and all solvent mixture proportions are by volume unless otherwise noted.

Example 1—Synthesis of MNP@Au Magneto-Plasmonic Nanoparticles

MNP@Au magneto-plasmonic nanoparticles were synthesized by the seeding approach discussed above.

Brown et al. (2000) synthesized large colloidal Au nanoparticles by growing small Au nanoparticles (seeds) with adding $HAuCl_4$ and citrate at boiling temperature. The surface-catalyzed reduction, which is the reduction of $Au^{3+}$ on the surface of seeds without new particle nucleation, allowed production of large Au nanoparticles with uniform size and shape.

By modifying this method, core-shell nanoparticles of magnetic nanoparticles core and Au shell have been synthesized by reducing $Au^{3+}$ on magnetic nanoparticle seeds. Because narrow size distribution of seeds is the key for monodispersity of MNP@Au, surface modification of MNPs was done with sodium citrate and aggregation was removed using a centrifuge prior to Au coating.

The average hydrodynamic size of citrate-coated MNPs (MNP-citrate) was 63±14 nm.

After citrate coating, additional sodium citrate was added to the MNP-citrate as a reducing agent and heated to boiling temperature, followed by the addition of Au ions. The clear brown color of MNPs became dark brown after addition of Au ions and gradually turned into red.

Example 2—Characterization of MNP@Au Magneto-Plasmonic Nanoparticles

Figure 1B:
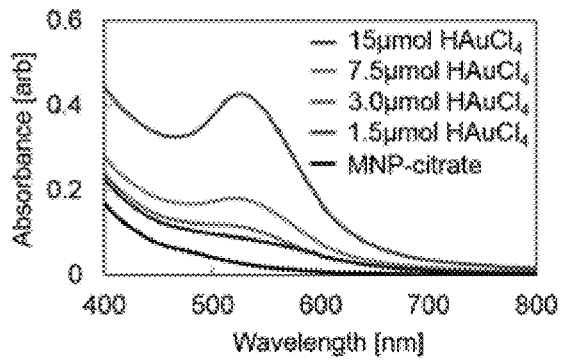
Figure 1C:
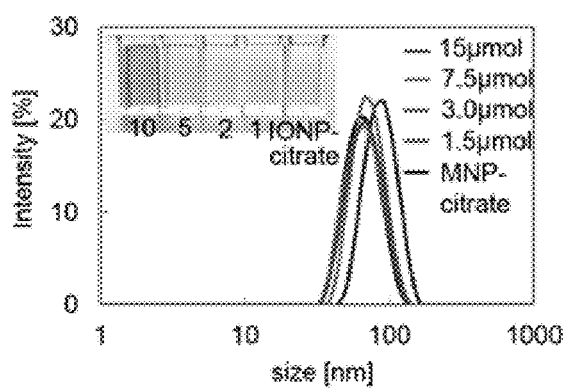

FIG. 1A-1C shows the Au-to-Fe weight ratio, absorbance, and hydrodynamic sizes of MNP-citrate and MNP@Au synthesized with initial $HAuCl_4$ varied from 1.5 to 15 µmol and fixed concentration of sodium citrate (5 mM). The color of MNP@Au changed from brown to red by increasing the amount of $HAuCl_4$ based on the absorbance of the particles. An increase in absorbance at the wavelength below 460 nm was observed for MNP-citrate, which corresponded with previous reports. It has been reported that iron oxides show absorption at the wavelength of 250-400 nm due to ligand to metal charge transition. The optical property of MNP@Au largely depends on the particle size, shape, and thickness of the Au shell due to surface plasmon resonance (SPR), which is based on the oscillation of free-electrons polarized to one surface under light with oscillation frequency. There were no apparent absorbance peaks for MNP-citrate and MNP@Au synthesized with 1 µmol $HAuCl_4$ at the wavelength above 460 nm. With increasing the amount of $HAuCl_4$, significant absorbance appeared at the wavelength between 460 nm and 600 nm. This can be explained by the increase of Au-to-Fe ratio proportionally with the amount of initial $HAuCl_4$. The peak of absorbance was observed at 526 nm for MNP@Au synthesized with 15 µmol $HAuCl_4$. Average hydrodynamic sizes of MNP@Au synthesized with 1.5, 3, 7.5, and 15 µmol $HAuCl_4$ were 84, 63, 61, and 57 nm, respectively.

TABLE 1

Synthesis conditions and characterizations of MNP@Au synthesized with initial $HAuCl_4$ of 15 µmol and sodium citrate concentration varied from 0.5 to 20 mM.

| Sodium citrate | $HAuCl_4$ | pH | Hydrodynamic size | SPR peak |
| --- | --- | --- | --- | --- |
| 20 mM | 15 µmol | 7.0 | 95 ± 31 nm | 531 nm |
| 5 mM | 15 µmol | 7.0 | 57 ± 26 nm | 526 nm |
| 2 mM | 15 µmol | 6.0 | Polydispersed | 523 nm |
| 1 mM | 15 µmol | 5.5 | polydispersed | 533 nm |
| 0.5 mM | 15 µmol | 3.2 | 64 ± 27 nm | 556 nm |

Figure 1D:
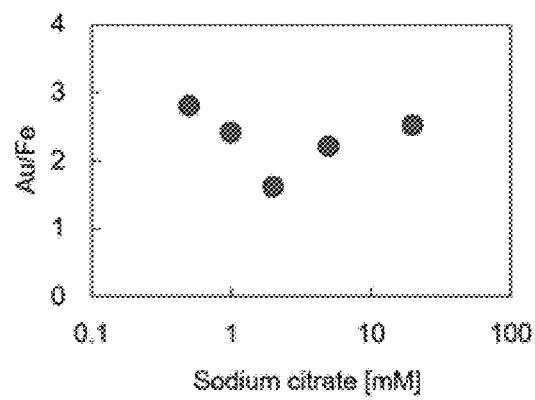
Figure 1E:
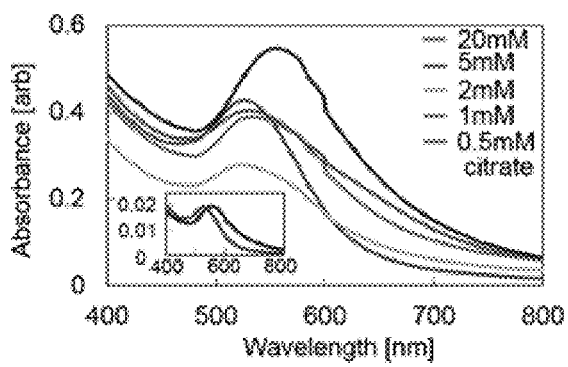
Figure 1F:
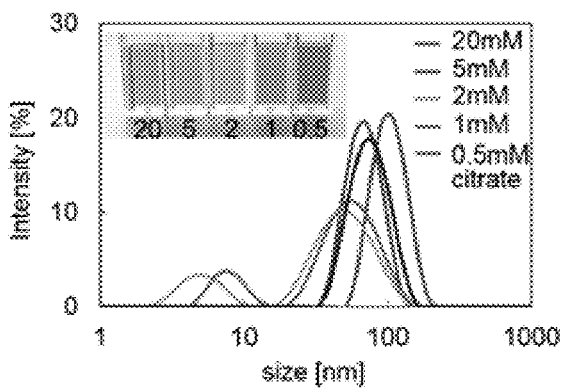

Table 1 shows synthesis conditions and characterizations of MNP@Au synthesized with initial $HAuCl_4$ of 15 µmol and sodium citrate concentration varied from 0.5 to 20 mM. FIG. 1D-1F illustrates the Au-to-Fe weight ratio, absorbance, and Au-to-Fe weight ratio of MNP@Au decreased significantly with increasing the concentration of sodium citrate from 0.5 mM to 2 mM and increased with further increases of sodium citrate. This indicates that the particle size of MNP@Au varies with the concentration of sodium citrate during synthesis. In FIG. 1C, MNP@Au synthesized with 0.5 mM sodium citrate showed SPR peak at the wavelength of 556 nm, and the absorbance at the SPR peak was the highest among other MNP@Au. Those synthesized with 1 mM and 20 mM sodium citrate showed broader SPR spectra, and similar broad SPR spectrum with lower absorbance was observed for those synthesized with 2 mM sodium citrate. MNP@Au synthesized with 5 mM sodium citrate showed a narrower SPR spectrum at the wavelength of 526 nm.

The citrate reduction method is the most commonly used method for gold nanoparticle synthesis. Typically, the nanoparticle size reduces with increasing sodium citrate concentration, and further increases of sodium citrate concentration increases the particle size. This trend corresponds with the reduced Au-to-Fe ratio with increasing sodium citrate concentration and increase of Au-to-Fe ratio with further increase of sodium citrate. This size variation with the concentration of sodium citrate has been determined by the solution pH during reaction which affects to the stability of nanoparticles and reactivity of Au (composition of $Au^{3+}$). The pKa value of citric acid is 3.2, 4.8, and 6.4. Above pH 6.4, the carboxyl groups in sodium citrate are fully deprotonated, and the resulting negative zeta potential keeps the stability of nanoparticles by repulsion. On the other hand, when the pH of reaction solution is low, the carboxyl groups are protonated, lose repulsion between nanoparticles, and consequently cause aggregation of nanoparticles. In reaction solutions with lower pH (pH 3.2 and 5.5 for 0.5 mM and 1 mM sodium citrate, respectively), it is possible that aggregation of nanoparticles occurred in the sodium citrate solution during growth of the Au shell, and the aggregation was reduced with increasing the sodium citrate concentration. The reduction of Au-to-Fe ratio with increasing sodium citrate concentration up to 2 mM can also be explained by pH dependent redox potential of Au complexes. $AuCl_4$ is faulted when $HAuCl_4$ is totally dissociated in aqueous solutions. As the solution pH increases, hydroxyl containing gold complexes are formed, and the complex changes from $AuCl_3(OH)^-$ to $Au(OH)^-$, which weakens reactivity. On the other hand, in the reaction solution with pH 7.0 (5 mM to 20 mM sodium citrate), it is possible that the reduction of $Au^{3+}$ was increased by increasing the amount of sodium citrate, which resulted in higher Au-to-Fe ratio.

In FIG. 1F, the average hydrodynamic sizes of MNP@Au synthesized with 0.5, 5, and 20 mM sodium citrate were 64, 57, and 95 nm, respectively, and MNP@Au synthesized with 1 and 2 mM sodium citrate showed polydispersity. The color of MNP@Au varied between purple and red. It is known that SPR is dependent on particle size, shape, dielectric properties, aggregate morphology, surface modification, and surrounding medium.[24] For example, the red shift and broadening of the absorbance have been reported as the hydrodynamic size of gold nanoparticles increases.[39] It is possible that the broad SPR peak of MNP@Au synthesized with 1 mM, 2 mM, and 20 mM sodium citrate is caused by their polydispersity or larger hydrodynamic size as compared to MNP@Au synthesized with 0.5 mM and 5 mM sodium citrate. As shown in FIG. 1E inset, MNP@Au synthesized with 5 mM sodium citrate exhibited the narrowest SPR peak at the wavelength of 526 nm, followed by MNP@Au synthesized with 0.5 mM sodium citrate, which showed highest SPR peak at wavelength of 556 nm. Hydrodynamic size is one of the important factors for nanoparticle-based in vivo applications. Nanoparticles smaller than 10 nm are rapidly removed by renal clearance, and larger nanoparticles (>200 nm) are removed by the reticuloendothelial system (RES) of the spleen and liver.[40] Therefore, the optimal hydrodynamic size of nanoparticle formulation for in vivo applications is known to be 10-100 nm.[41] This excludes MNP@Au synthesized with 1 mM and 2 mM sodium citrate, which showed multiple peaks in their hydrodynamic sizes, and MNP@Au synthesized with 20 mM sodium citrate, which showed hydrodynamic size distribution between 51 nm to 220 nm. Comparing MNP@Au synthesized with 0.5 mM and 5 mM sodium citrate, serious aggregation was observed for MNP@Au synthesized with 0.5 mM sodium citrate within a month after synthesis, while MNP@Au synthesized with 5 mM sodium citrate remained stable. Considering these factors, we conducted further characterization on the MNP@Au synthesized with 15 μmol $HAuCl_4$ and 5 mM sodium citrate.

FIG. 2A shows the TEM image of the MNP@Au. The average particle diameter of 14.5 nm and spherical morphology were observed from this TEM image. Because the MNP core showed an average diameter of 10 nm and spherical morphology in our previous report, the average thickness of the shell is calculated to be 2.3 nm.

FIG. 2B shows the X-ray diffraction (XRD) pattern of MNP@Au. The XRD pattern of MNP@Au showed sharp peaks at 38.2°, 44.4°, 64.5°, and 77.7°, which can be indexed to the (1 1 1), (2 0 0), (2 2 0) and (3 1 1) planes, respectively. The sharp peak at 38.2° could be the synergistic effect from (3 1 1) plane of MNP core and (1 1 1) plane of Au shell. The diffraction from the core can be observed by the penetration of X-ray through the gold shell layer, and the diffraction from the gold shell dominates as the thickness of the gold shell increases.

FIGS. 2C and 2D show the magnetization curves of MNP-citrate and MNP@Au, and the picture of MNP@Au attracted by a magnet. The MNPs showed superparamagnetic properties before and after Au coating. The saturation magnetization of MNP-citrate and MNP@Au were 27 emu/g and 22 emu/g, which are 36% and 29% of the bulk saturation value for hematite (76 $Am^2$/kg or emu/g), respectively. Significant decrease in saturation magnetization of MNPs after Au coating due to diamagnetic contribution of the Au shell is observed. However, MNP@Au showed slightly lower saturation magnetization and higher susceptibility compared to MNP-citrate, contrary to the large portion of Au (61%) in MNP@Au. Because magnetic nanoparticles respond to the magnetic field gradient in a size dependent manner, magnetic separation has been used to separate larger particles. We expect that MNP@Au with small saturation magnetization was removed during purification process using a magnet, and MNP@Au with only large magnetization was collected after purification.

Example 3—Multimodal Imaging Property of MNP@Au Magneto-Plasmonic Nanoparticles

MRI and micro-CT scan were conducted to demonstrate multimodal imaging capability of MNP@Au magneto-plasmonic nanoparticles. FIGS. 3A and 3B show the $T_2$-weighted MR images and transverse relaxivity of MNP@Au as a function of Fe concentration. Stronger negative contrast was observed with increasing the concentration of Fe. In addition, linear correlation between transverse relaxivity and Fe concentration was observed. The $T_2$ relaxivity was calculated to be 317 $mM^{-1} \cdot s^{-1}$.

The micro-CT images and CT values of MNP@Au are shown in FIGS. 3C and 3D. The brightness increased in a concentration-dependent manner, and MNP@Au showed CT attenuation values of 24 Hounsfield units (HU) and 178 HU at the concentrations of 0.5 mg/ml and 5 mg/ml, respectively. This result corresponded to previous reports showing the concentration dependence of CT value from Au nanoparticles due to X-ray attenuation of gold. There is a growing interest in using Au nanoparticles as CT contrast agents because of the higher X-ray attenuation coefficient of gold compared to iodine which is currently used in the clinic. Because X-ray attenuation is not efficient and the blood circulation time of iodinated CT contrast agents is short, the nanoparticles containing heavy metal are the great candidates as novel CT contrast agents. These strong contrasts in MRI and X-ray CT from MNP@Au suggest that the magneto-plasmonic nanoparticles can be used as multimodal imaging probes for MRI and X-ray CT.

Example 4—Cytotoxicity of MNP@Au and MNP@Au-PEG

Figure 4A:
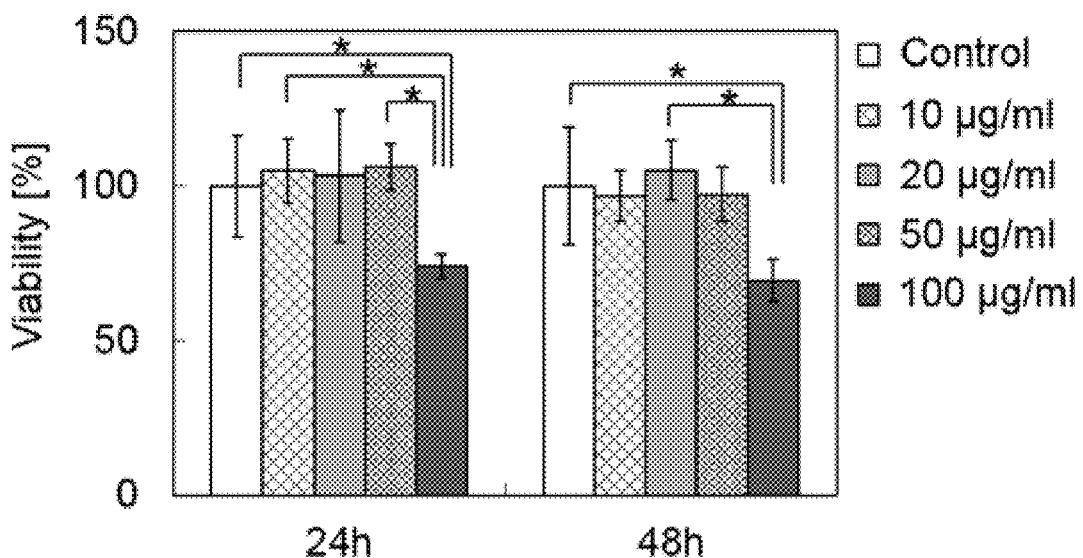
FIGS. 4A-4B. Viability of human primary astrocytes after 24 h and 48 h exposure to MNP@Au (4A) and MNP@Au-PEG (4B; PEG: poly(ethylene glycol)) determined using XTT assay. (* p<0.05; NS, not significant, p>0.05; N=3) Viability reduction was observed after exposing MNP@Au at the concentration of 100 µg/ml. In contrast, no reduction was observed for the astrocytes exposed to PEG coated MNP@Au.
Figure 4B:
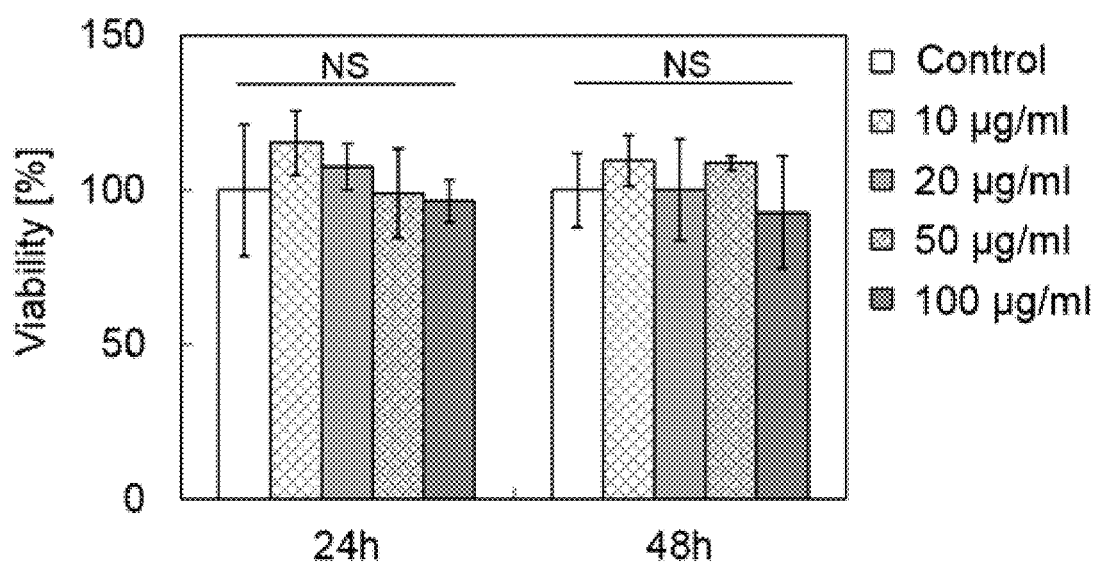

FIGS. 4A-4B shows the impacts of MNP@Au and MNP@Au-PEG on cell viability evaluated by XTT assay. The viability of human astrocytes decreased to 74% and 69% after exposure of MNP@Au at the concentration of 100 μg/ml for 24 h and 48 h, respectively. No significant decrease in the viability was observed for the cells exposed to MNP@Au-PEG at the concentrations lower than 100 µg/ml.

Although magneto-plasmonic nanoparticles have been studied for biosensor applications, they are relatively new in in vitro and in vivo biomedical applications. Thus, there are fewer studies evaluating the biocompatibility of MNP@Au nanoparticles compared to well-studied iron oxide nanoparticles and gold nanoparticles. Moreover, viability study on primary human astrocyte cells is not conducted. Viability assays on cell lines including L929 fibroblast, HeLa cells, H9c2 cardiomyoblasts, and MCF-7 breast carcinoma cells after exposing MNP@Au are conducted. Significant viability reduction was not observed in L929 fibroblast and HeLa cells, and 14% and 23% reductions were observed in cultured H9c2 cardiomyoblasts and MCF-7 breast carcinoma cells after 24 h exposure of nanoparticles at the concentration of 500 µg/ml. This reduction range is similar results on primary human astrocytes. Also, no significant influence on the viability of human mesenchymal stem cells (hMSCs) and U87 glioma cells has been reported after exposing hybrid nanoparticles containing $Fe_3O_4$ core coated with gold nanoparticles. Because MNP@Au is less stable in media due to lack of PEG chain, we expect that aggregation of MNP@Au caused the reduction of viability contrary to the PEG-coated MNP@Au which showed no viability reduction.

Example 5—In Vitro BBB Model

The transmigration efficiency of magneto-plasmonic nanoparticles was evaluated using the in vitro BBB model prepared with primary human brain microvascular endothelial cells (HBMECs) and human astrocytes (HAs) (FIG. 5A). MNP@Au-PEG were used for this experiment due to their high viability and stability in media. The transmigration efficiency of magneto-plasmonic nanoparticles was determined by measuring the concentration of the nanoparticles crossed the in vitro BBB model. The transmigration efficiency of the nanoparticles in the absence and in the presence of a magnetic field is shown in FIG. 5B. Only 3.8% of the nanoparticles were able to cross the BBB without a magnetic field. Compared to this low transmigration efficiency due to the high integrity of the BBB, the presence of a magnetic field increased transmigration efficiency significantly which was four-fold increase compared to the transmigration in the absence of a magnetic field.

The integrity of the BBB model was evaluated by TEER measurement. FIG. 5C shows TEER values of the control BBB without nanoparticles or a magnetic field from a magnet, with nanoparticles in the absence of a magnetic field, and with nanoparticles in the presence of a magnetic field from a magnet. Because a TEER value around 200 $\Omega/cm^2$ is considered as the formation of the BBB, 195.5±13.0 $\Omega/cm^2$ from the control BBB proves that the BBB model is already formed and intact. The TEER values of the BBB with nanoparticles in the absence and in the presence of a magnetic field were 194.2±5.2 and 197.7±4.7 $\Omega/cm^2$, respectively. Compared to the control BBB, there was no effect on the integrity of the BBB model after exposure to nanoparticles and magnetic field.

Figure 5D:
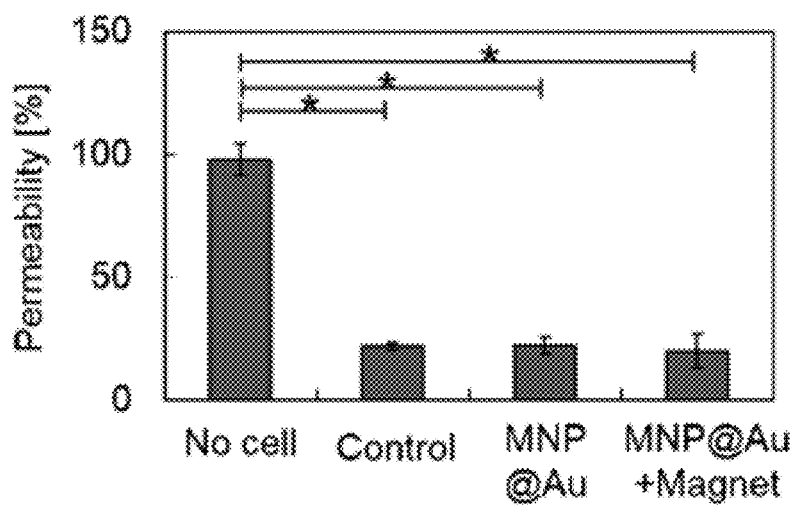
Figure 6:
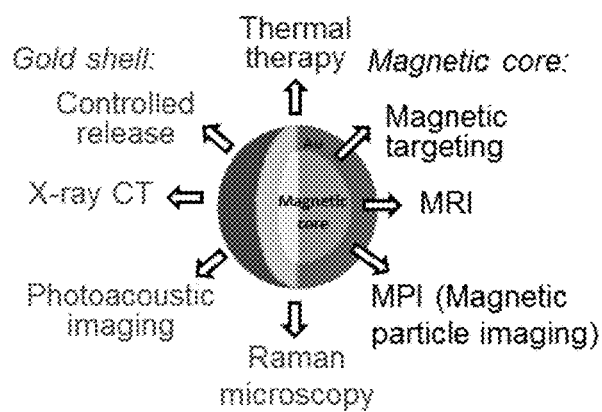
FIG. 6. Magneto-plasmonic nanoparticles have multi-functionality that works in both stimuli-responsive cargos and imaging probes for multiple imaging systems including MRI, X-ray CT, MPI (magnetic particle imaging), photoacoustic imaging, and Raman microscopy. Multimodal imaging enables accurate diagnostics by overcoming disadvantages of each imaging modality.
Figure 7:
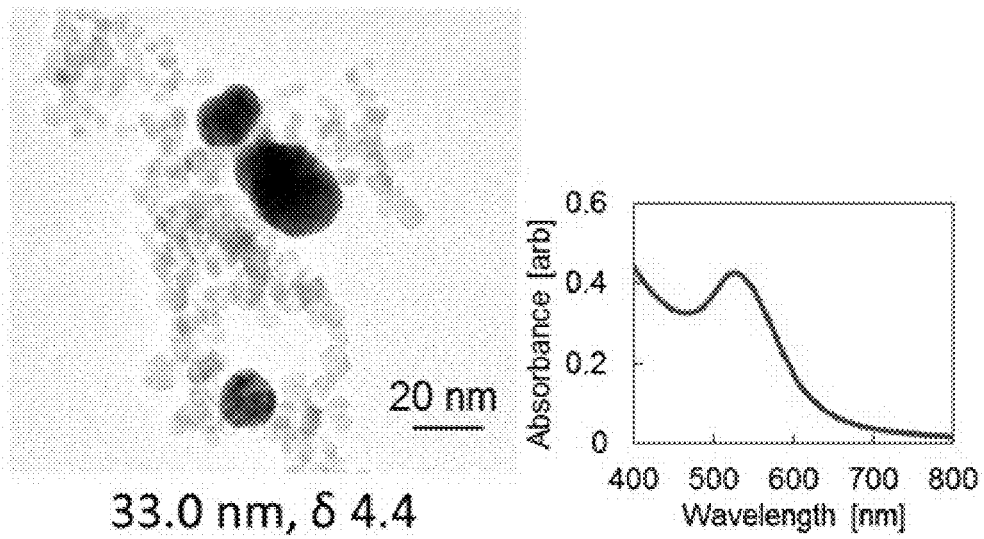
FIG. 7. Magneto-plasmonic nanoparticles with two different structures were synthesized. MNP@Au contains iron oxide core and Au shell (sphere shape) and shows surface plasmon resonance (SPR) peak in visible light range. MNP@Au has been applied for biosensors, photothermal therapy, and some of the imaging applications (MRI, X-ray CT).
Figure 8:
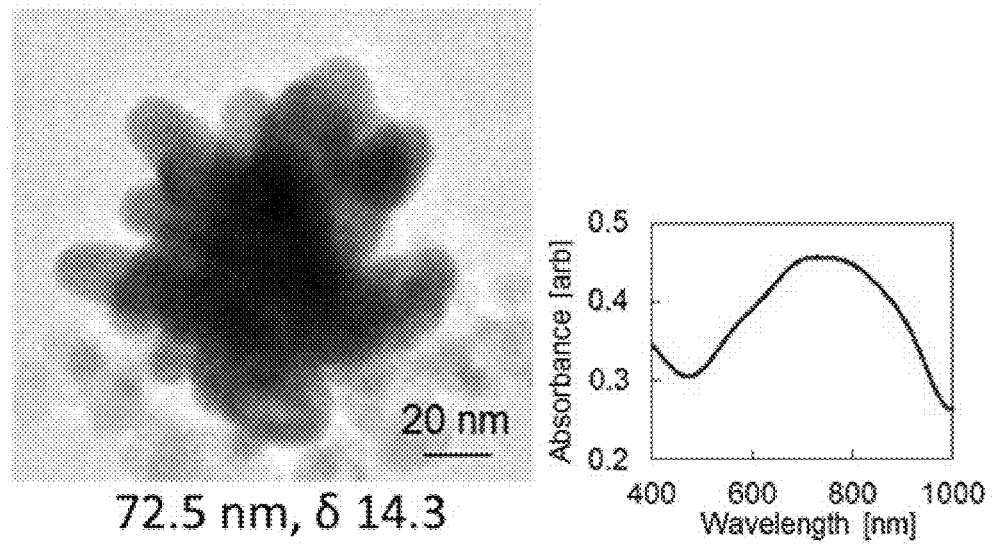
FIG. 8. Magneto-gold nanostar has iron oxide core and Au nanostar shell, and shows SPR peak in near infrared (NIR) region. Because the penetration of NIR is greater than visible light, magneto-gold nanostar is suitable for optical imaging systems and controlled drug release using NIR.
Figure 9:
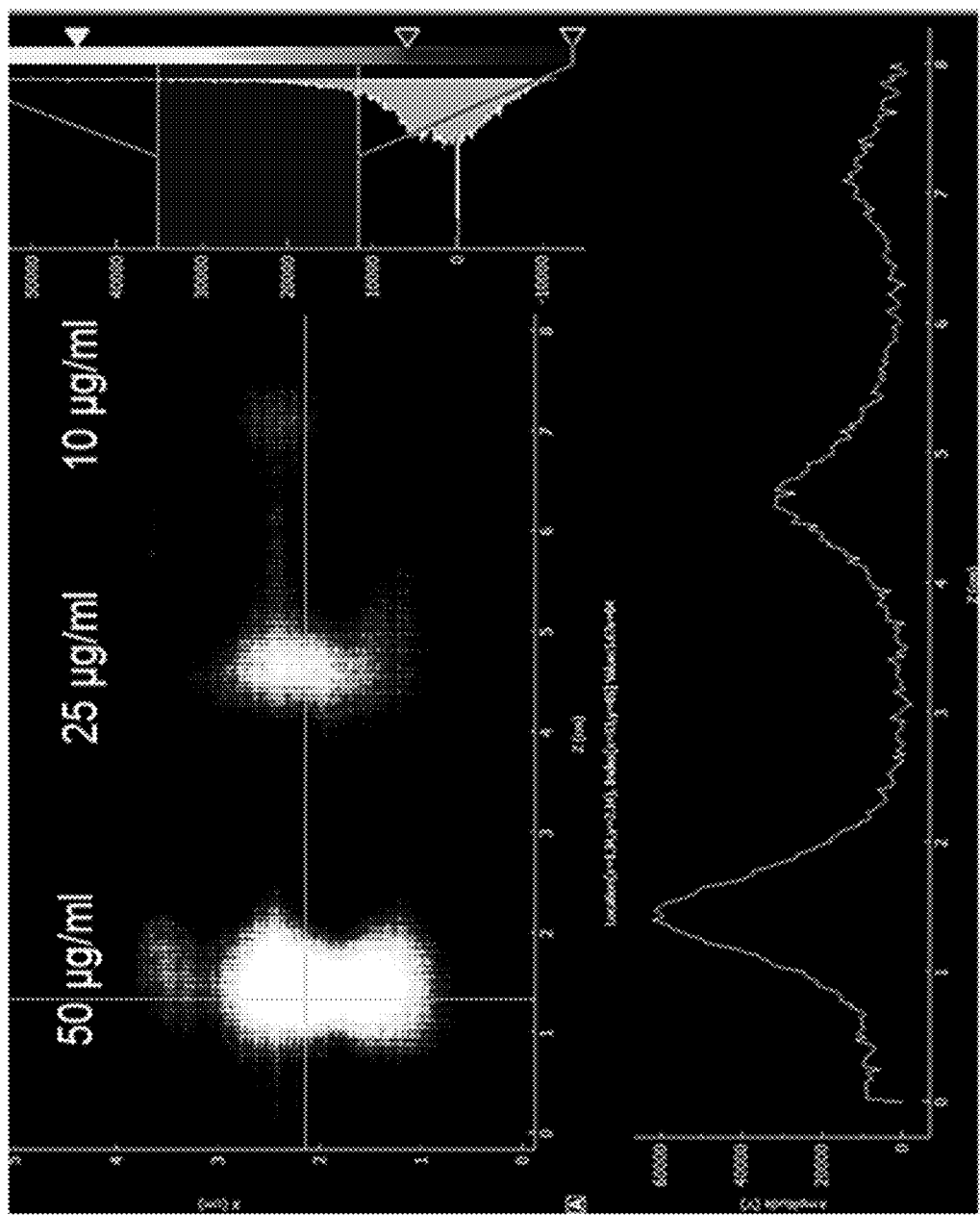
FIG. 9. MPI images of MNP@Au encapsulated inside liposome. The concentration of MNP@Au was varied from 10 to 50 μg/ml. The stronger signal was observed with increasing concentration of MNP@Au.
Figure 9:
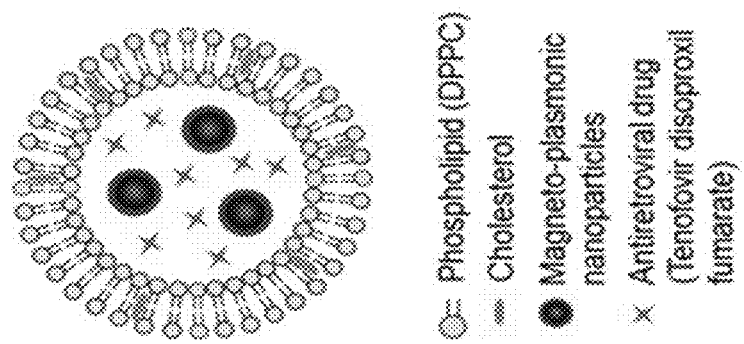
Figure 10A:
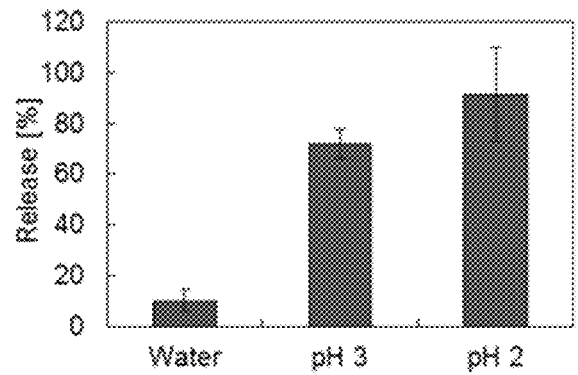
FIGS. 10A-10C. Stimuli-responsive drug release of MNP@Au and magneto-plasmonic nanostar. Release of doxorubicin from MNP@Au in acidic pH was confirmed (10A). 72% and 91% of doxorubicin was released in pH 2 and 3, respectively. Release of Tenofovir from magneto-gold nanostar was triggered by heat (10B). Drug release was confirmed at 50, 60, and 70° C., and release rate was increased by time (10C).
Figure 10B:
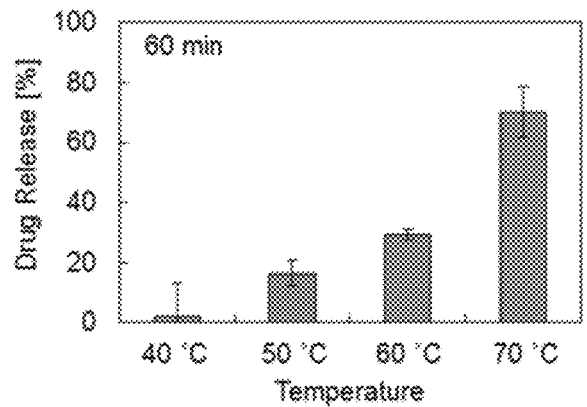
Figure 10C:
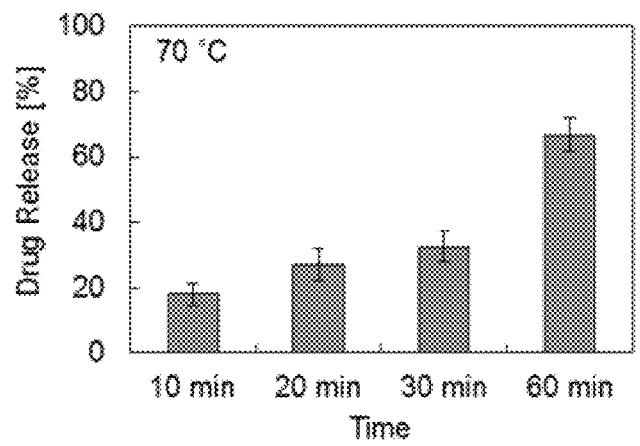

Permeability across the BBB model was then determined by measuring the transfer of FITC-dextran. FIG. 5D shows the percentage of FITC-dextran transfer across the BBB calculated with respect to the FITC-dextran transfer across untreated insert without cells. The FITC-dextran transfer of the control BBB, the BBB with nanoparticles in the absence of a magnetic field, and the BBB with nanoparticles in the presence of a magnetic field was 22%, 22%, and 20%, respectively. This shows that exposing nanoparticles along with an external magnetic field does affect the permeability of the BBB. Overall, FIG. 5A-5D indicates that the presence of a magnetic field increases the transmigration of magneto-plasmonic nanoparticles significantly without affecting the integrity and permeability of the BBB.

As such, the nanoparticles described herein demonstrate biocompatibility and capability to cross the BBB and these nanoparticles can be used for image-guided therapy for diseases including, but not limited to, brain diseases. The MRI and X-ray CT contrasts generated by the magneto-plasmonic nanoparticles will enable image-guided therapy for diseases such as brain tumors, Alzheimer's disease, and human immunodeficiency virus (HIV) infection. Furthermore, the magneto-plasmonic nanoparticles can be used for a wide range of biomedical applications including hyperthermia or photothermal therapy, radiation sensitizer, and stem cell tracking.

REFERENCES

1. P. Ballabh, A. Braun and M. Nedergaard, *Neurobiol. Dis.*, 2004, 16, 1-13.
2. M. Nair, R. D. Jayant, A. Kaushik and V. Sagar, *Adv. Drug Deliv. Rev.*, 2016, 103, 202-217.
3. Kaushik, R. Dev Jayant, V. Sagar and M. Nair, *Expert Opin. Drug Deliv.*, 2014, 11, 1635-1646.
4. R. D. Jayant, D. Sosa, A. Kaushik, V. Atluri, A. Vashist, A. Tomitaka and M. Nair, *Expert Opin. Drug Deliv.*, 2016, in print.
5. S. Ohtsuki and T. Terasaki, *Pharm. Res.*, 2007, 24, 1745-1758.
6. S. Wohlfart, S. Gelperina and J. Kreuter, *J. Control. Release*, 2012, 161, 264-273.
7. Q. A. Pankhurst, J. Connolly, S. K. Jones and J. Dobson, *J. Phys. D. Appl. Phys.*, 2003, 36, 167-181.
8. R. E. E. Rosensweig, *J. Magn. Magn. Mater.*, 2002, 252, 370-374.
9. M. A. Abakumov, N. V. Nukolova, M. Sokolsky-Papkov, S. A. Shein, T. O. Sandalova, H. M. Vishwasrao, N. F. Grinenko, I. L. Gubsky, A. M. Abakumov, A. V. Kabanov and V. P. Chekhonin, *Nanomedicine Nanotechnology, Biol. Med.*, 2015, 11, 825-833.
10. A. Tomitaka, J. Jo and I. Aoki, *Inflamm. Regen.*, 2014, 34, 45-55.
11. J. Chen, M. Shi, P. Liu, A. Ko, W. Zhong, W. Liao and M. M. Q. Xing, *Biomaterials*, 2014, 35, 1240-1248.
12. R. D. Jayant, V. S. R. Atluri, M. Agudelo, V. Sagar, A. Kaushik and M. Nair, *Int. J. Nanomedicine*, 2015, 10, 1077-1093.
13. D. Kami, T. Kitani, T. Kishida, O. Mazda, M. Toyoda, A. Tomitaka, S. Ota, R. Ishii, Y. Takemura, M. Watanabe, A. Umezawa and S. Gojo, *Nanomedicine*, 2014, 10, 1165-74.
14. R. Y. Huang, P. H. Chiang, W. C. Hsiao, C. C. Chuang and C. W. Chang, *Langmuir*, 2015, 31, 6523-6531.
15. A. Tomitaka, K. Ueda, T. Yamada and Y. Takemura, *J. Magn. Magn. Mater.*, 2012, 324, 3437-3442.
16. Tomitaka, T. Yamada and Y. Takemura, *J. Nanomater.*, 2012, 2012, 1-5.
17. Tassa, S. Y. Shaw and R. Weissleder, *Acc. Chem. Res.*, 2011, 44, 842-852.
18. S. Tong, S. Hou, Z. Zheng, J. Zhou and G. Bao, *Nano Lett.*, 2010, 10, 4607-4613.

19. H. Yang, Y. Zhuang, Y. Sun, A. Dai, X. Shi Xiangyang, D. Wu, F. Li, H. Hu and S. Yang, *Biomaterials*, 2011, 32, 4584-4593.
20. K. K. Cheng, P. S. Chan, S. Fan, S. M. Kwan, K. L. Yeung, Y. X. J. Wang, A. H. L. Chow, E. X. Wu and L. Baum, *Biomaterials*, 2015, 44, 155-172.
21. H. Ding, V. Sagar, M. Agudelo, S. Pilakka-Kanthikeel, V. S. R. Atluri, A. Raymond, T. Samikkannu and M. P. Nair, *Nanotechnology*, 2014, 25, 055101.
22. A. Kaushik, R. D. Jayant, R. Nikkhah-Moshaie, V. Bhardwaj, U. Roy, Z. Huang, A. Ruiz, A. Yndart, V. Atluri, N. El-Hage, K. Khalili and M. Nair, *Sci. Rep.*, 2016, 6, 25309.
23. S. Eustis and M. a el-Sayed, *Chem. Soc. Rev.*, 2006, 35, 209-217.
24. S. Zeng, K.-T. Yong, I. Roy, X.-Q. Dinh, X. Yu and F. Luan, *Plasmonics*, 2011, 6, 491-506.
25. Y. Li, H. J. Schluesener and S. Xu, *Gold Bull.*, 2010, 43, 29-41.
26. L. V. Wang and S. Hu, *Science* (80-.), 2012, 335, 1458-1462.
27. Xu, G. A. Tung and S. Sun, *Chem Mater.*, 2008, 20, 4167-4169.
28. L. C. Kennedy, L. R. Bickford, N. A. Lewinski, A. J. Coughlin, Y. Hu, E. S. Day, J. L. West and R. A. Drezek, *Small*, 2011, 7, 169-183.
29. J. Lin, W. Zhou, A. Kumbhar, J. Wiemann, J. Fang, E. E. Carpenter and C. J. O'Connor, *J. Solid State Chem.*, 2001, 159, 26-31.
30. J. L. Lyon, D. A. Fleming, M. B. Stone, P. Schiffer and M. E. Williams, *Nano Lett.*, 2004, 4, 719-723.
31. Y. Xing, Y.-Y. Jin, J.-C. Si, M.-L. Peng, X.-F. Wang, C. Chen and Y.-L. Cui, *J. Magn. Magn. Mater.*, 2014, 380, 150-156.
32. K. R. Brown, D. G. Walter and M. J. Natan, *Chem. Mater.*, 2000, 12, 306-313.
33. K. R. Brown and M. J. Natan, *Langmuir*, 1998, 14, 726-728.
34. T. T. Hien Pham, C. Cao and S. J. Sim, *J. Magn. Magn. Mater.*, 2008, 320, 2049-2055.
35. F. N. Sayed and V. Polshettiwar, *Sci. Rep.*, 2015, 5, 9733.
36. G. Frens, *Nat. Phys. Sci.*, 1973, 241, 20-22.
37. X. Ji, X. Song, J. Li, Y. Bai, W. Yang and X. Peng, *J. Am. Chem. Soc.*, 2007, 129, 13939-13948.
38. V. Goia and E. Matijević, *Colloids Surfaces A Physicochem. Eng. Asp.*, 1999, 146, 139-152.
39. J. Nam, N. Won, H. Jin, H. Chung and S. Kim, *J. Am. Chem. Soc.*, 2009, 131, 13639-13645.
40. A. K. Gupta and M. Gupta, *Biomaterials*, 2005, 26, 3995-4021.
41. Z. Wilczewska, K. Niemirowicz, K. H. Markiewicz and H. Car, *Pharmacol. Reports*, 2012, 64, 1020-1037.
42. M. Mandal, S. Kundu, S. K. Ghosh, S. Panigrahi, T. K. Sau, S. M. Yusuf and T. Pal, *J. Colloid Interface Sci.*, 2005, 286, 187-194.
43. Z. Xu, Y. Hou and S. Sun, *J. Am. Chem. Soc.*, 2007, 129, 8698-8699.
44. A. E. Berkowitz, W. J. Schuele and P. J. Flanders, *J. Appl. Phys.*, 1968, 39, 1261-1263.
45. C. T. Yavuz, J. T. Mayo, W. W. Yu, A. Prakash, J. C. Falkner, S. Yean, L. Cong, H. J. Shipley, A. Kan, M. Tomson, D. Natelson and V. L. Colvin, *Science*, 2006, 314, 964-947.
46. L. Jing, X. Liang, Z. Deng, S. Feng, X. Li, M. Huang, C. Li and Z. Dai, *Biomaterials*, 2014, 35, 5814-5821.
47. H. Xing, W. Bu, S. Zhang, X. Zheng, M. Li, F. Chen, Q. He, L. Zhou, W. Peng, Y. Hua and J. Shi, *Biomaterials*, 2012, 33, 1079-1089.
48. N. Lee, S. H. Choi and T. Hyeon, *Adv. Mater.*, 2013, 25, 2641-2660.
49. Y. Li, J. Liu, Y. Zhong, J. Zhang, Z. Wang, L. Wang, Y. An, M. Lin, Z. Gao and D. Zhang, *Int. J. Nanomedicine*, 2011, 6, 2805-19.
50. J. Salado, M. Insausti, L. Lezama, I. Gil de Muro, M. Moros, B. Pelaz, V. Grazu, J. M. de la Fuente and T. Rojo, *Nanotechnology*, 2012, 23, 315102.
51. Mohammad, G. Balaji, A. Weber, R. M. Uppu and C. S. S. R. Kumar, *J. Phys. Chem. C. Nanomater. Interfaces*, 2010, 114, 19194-19201.
52. J. Ren, S. Shen, Z. Pang, X. Lu, C. Deng and X. Jiang, *Chem. Commun.*, 2011, 47, 11692.
53. S. Narayanan, B. N. Sathy, U. Mony, M. Koyakutty, S. V. Nair and D. Menon, *ACS Appl. Mater. Interfaces*, 2012, 4, 251-260.
54. V. Zlokovic, *Neuron*, 2008, 57, 178-201.
55. Wilhelm, C. Fazakas and I. A. Krizbai, *Acta Neurobiol Exp*, 2011, 71, 113-128.
56. D. Raymond, P. Diaz, S. Chevelon, M. Agudelo, A. Yndart-Arias, H. Ding, A. Kaushik, R. D. Jayant, R. Nikkhah-Moshaie, U. Roy, S. Pilakka-Kanthikeel and M. P. Nair, *J. Neurovirol.*, 2016, 22, 129-139.

We claim:

1. Magneto-plasmonic nanostars, having a magnetic core of iron oxide and a gold shell, synthesized by a method comprising the steps of:
   a) contacting iron oxide nanoparticles with an acid and, optionally, sonicating the resultant mixture the iron oxide core having a hydrodynamic size between 49 nm and 77 nm;
   b) adding a reducing agent to the mixture produced in step a) to coat iron oxide nanoparticles with the reducing agent and optionally, sonicating the resultant mixture;
   c) washing and separating the coated iron oxide nanoparticles from the mixture produced in step b);
   d) dispersing and sonicating the coated iron oxide nanoparticles produced in step c) in a solution of reducing agent and heating the resulting mixture to boiling temperature, optionally, with stirring;
   e) adding a gold precursor to the mixture produced in step d) to produce magnetic core/gold shell nanoparticles (MNP@Au) with the magnetic core being the coated iron oxide nanoparticles, and MNP@Au having a hydrodynamic size of 51 nm to 220 nm, the MNP@Au having an average shell thickness of 2.3 nm;
   f) dispersing the MNP@Au in a solution consisting of $HAuCl_4$ aqueous solution;
   g) adding silver nitrate to the solution of step f);
   h) adding an acid to the mixture of step g); and
   i) neutralizing the solution of step h) with a base;
   said nanostars having a single surface plasmon resonance (SPR) peak being about 700 nm to about 750 nm, and said nanostars are bound to a therapeutic agent, the agent being capable of being released from the nanostars by applying a near-infrared light source.

2. A method of treating a disease in a subject, the method comprising the steps of:
   i) administering to the subject a formulation comprising magneto-plasmonic nanostars of claim 1; and
   ii) applying an alternating current magnetic field to the subject to induce local electric charge oscillations in the MNP@Au to release the therapeutic agent.

3. The method of claim 2, wherein the nanostars are capable of releasing the MNP@Au and the therapeutic agent when subjected to changes in one or more of the following stimuli: alternating current magnetic field, near-infrared light, pH, and temperature.

4. A method of visualizing a target site in a subject, the method comprising the steps of:
   i) administering to the subject magneto-plasmonic nanostars of claim 1; and
   ii) visualizing the target site by applying to the target site one or more of the following: magnetic field, X-rays, and non-ionizing radiation.

5. The magneto-plasmonic nanostars of claim 1, wherein the acid of step a) is selected from hydrochloric acid, acetic acid, and sulfuric acid.

6. The magneto-plasmonic nanostars of claim 1, wherein the reducing agent is selected from sodium citrate, ascorbic acid, sodium borohydride, and polyvinyl pyrrolidine.

7. The magneto-plasmonic nanostars of claim 1, wherein the gold precursor is selected from $HAuCl_4$, $AuCl_3$, and $Au(OH)_3$.

8. The magneto-plasmonic nanostars of claim 1, wherein in step d) the reducing agent is used at a concentration between 0.5 mM and 20 mM and in step e) the gold precursor is used at a concentration between 1.5 µM and 15 µM.

9. The magneto-plasmonic nanostars of claim 1, the method further comprising isolating MNP@Au produced at the end of step e) by administering a magnetic field and washing the isolated MNP@Au.

10. The magneto-plasmonic nanostars of claim 1, the method further comprising binding the nanostars to a therapeutic agent via one or more of the following molecular interactions: ionic bond, electrostatic attraction, gold-sulfur bond, and metal-phosphate bond.

11. The magneto-plasmonic nanostars of claim 1, the method further comprising encapsulating the nanostars bound to the therapeutic agent within liposomes, wherein the liposomes comprise lipids and optionally cholesterol.

12. The magneto-plasmonic nanostars of claim 1, the method further comprising modifying the nanostars with a coating comprising thiol molecules.

13. The magneto-plasmonic nanostars of claim 12, wherein the coating comprises one or more of the following: PEG-SH, HS-PEG-COOH, HS-PEG-$NH_2$, 11-Mercaptoundecanoic acid, and peptides comprising thiol molecules.

14. A magnetic core/gold shell nanoparticle, comprising an iron oxide core having a hydrodynamic size between 49 nm and 77 nm;
   a shell covering the iron oxide core,
   in which the shell comprises gold; and
   a therapeutic agent bonded to the shell,
   in which the magnetic core/gold shell nanoparticle is a nanostar having a single SPR peak being about 700 nm to about 750 nm, and the therapeutic agent is capable of being released from the nanostars by applying a near-infrared light source; and
   the nanostars bound to the therapeutic agent being encapsulated within liposomes, the liposomes comprising lipids and cholesterol, the therapeutic agent to lipid ratio being from 0.1:34 to 1:34.

15. The magnetic core/gold shell nanoparticle of claim 14, in which the nanoparticle is coated with thiol PEG, PEG-SH, HS-PEG-COOH, HS-PEG-$NH_2$, 11-Mercaptoundecanoic acid, or thiol-containing peptides.

16. The magneto-plasmonic nanostars of claim 1, in step d) the solution of reducing agent having an acidic pH.

17. The magneto-plasmonic nanostars of claim 16, the acidic pH being 3.2, 5.5 or 6.

18. The magneto-plasmonic nanostars of claim 11, the nanostars bound to the therapeutic agent within liposomes having a therapeutic agent to lipid ratio from 0.1:34 to 1:34.

19. The magneto-plasmonic nanostars of claim 1, step h) having a reaction time of 1 min.

\* \* \* \* \*